United States Patent
Cotton et al.

(10) Patent No.: US 10,209,235 B2
(45) Date of Patent: Feb. 19, 2019

(54) SENSING AND SURFACING OF CROP LOSS DATA

(71) Applicant: Deere & Company, Moline, IL (US)

(72) Inventors: Alexander Cotton, Cedar Rapids, IA (US); Steven R. Kingsley, Cedar Falls, IA (US)

(73) Assignee: Deere & Company, Moline, IL (US)

(*) Notice: Subject to any disclaimer, the term of this patent is extended or adjusted under 35 U.S.C. 154(b) by 375 days.

(21) Appl. No.: 14/703,131

(22) Filed: May 4, 2015

(65) Prior Publication Data

US 2016/0327535 A1 Nov. 10, 2016

(51) Int. Cl.
*A01D 41/127* (2006.01)
*G01N 33/00* (2006.01)

(52) U.S. Cl.
CPC ..... *G01N 33/0098* (2013.01); *A01D 41/1273* (2013.01)

(58) Field of Classification Search
CPC .......... A01D 41/1271; A01D 41/1273; G01N 33/0098; G01N 33/025
See application file for complete search history.

(56) References Cited

U.S. PATENT DOCUMENTS

| 6,778,894 | B2 | 8/2004 | Beck | |
| 7,485,035 | B1* | 2/2009 | Yde | A01F 12/40 460/111 |
| 8,406,964 | B2* | 3/2013 | Baumgarten | A01D 41/127 700/83 |
| 2011/0304626 | A1* | 12/2011 | Fotev | G06F 17/246 345/428 |
| 2015/0138205 | A1* | 5/2015 | Rajagopalan | A61B 5/742 345/440 |

FOREIGN PATENT DOCUMENTS

EP 2681984 A1 1/2014

* cited by examiner

*Primary Examiner* — Stephen W Smoot
(74) *Attorney, Agent, or Firm* — Joseph R. Kelly; Kelly, Holt & Christenson PLLC

(57) ABSTRACT

A crop loss level generator receives a crop loss sensor signal from a crop loss sensor and generates a crop loss metric indicative of a sensed crop loss level based on the crop loss sensor signal. A first crop loss display generator generates a first crop loss display element based on the crop loss metric and controls a display device to display the first crop loss display element relative to a target loss range indicator indicative of a target loss range. A historic crop loss display generator generates a historic crop loss display element, based on previously generated crop loss metrics, and controls the display device to display the historic crop loss display element relative to the target loss indicator and relative to the first crop loss display element.

15 Claims, 25 Drawing Sheets

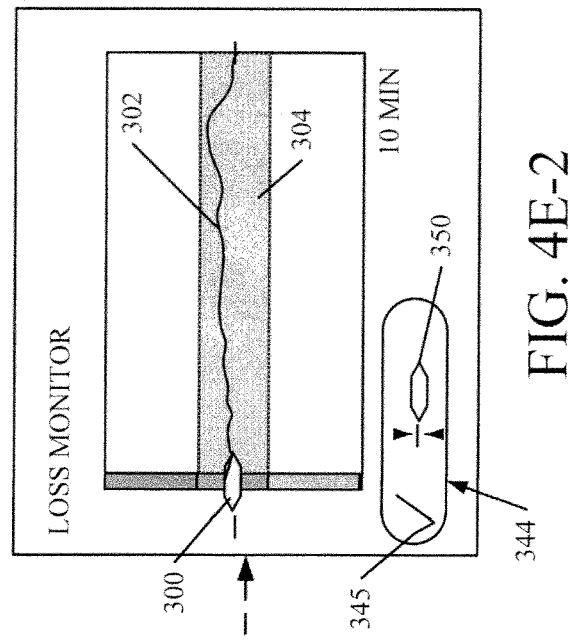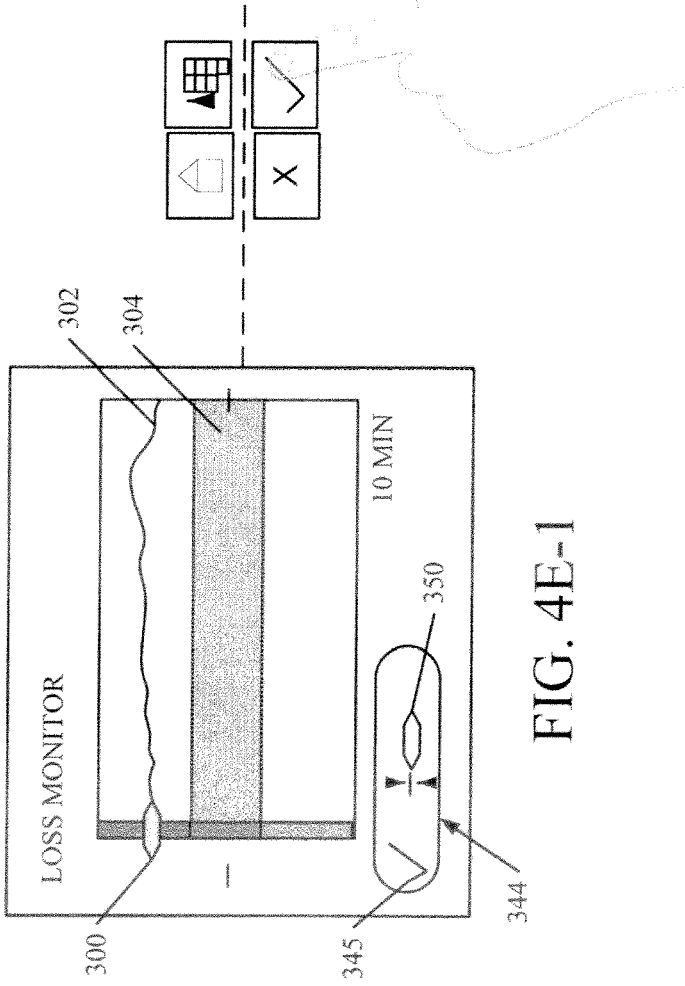
FIG. 4E-1
FIG. 4E-2

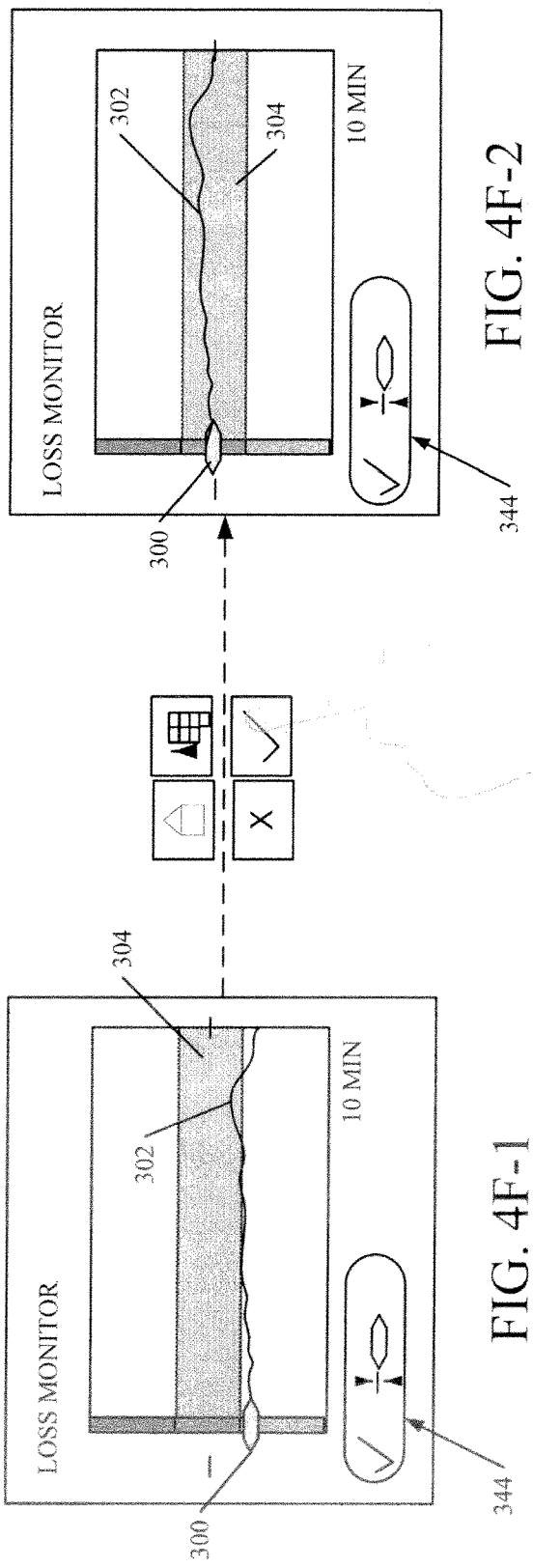

US 10,209,235 B2

SENSING AND SURFACING OF CROP LOSS DATA

FIELD OF THE DESCRIPTION

The present invention relates to agricultural equipment. More specifically, the present invention relates to crop harvesting.

BACKGROUND

There are a wide variety of different types of harvesting machines. Such machines can include combines and other harvesting equipment.

It is common for such harvesting equipment to include loss sensors that sense some type of metric that can be indicative of the amount of the harvested crop being lost during the harvesting operation. For instance, grain harvesting equipment often includes a grain loss monitoring system that has a set of sensors that monitor grain loss from various parts of the harvester.

The discussion above is merely provided for general background information and is not intended to be used as an aid in determining the scope of the claimed subject matter.

SUMMARY

A crop loss level generator receives a crop loss sensor signal from a crop loss sensor and generates a crop loss metric indicative of a sensed crop loss level based on the crop loss sensor signal. A first crop loss display generator generates a first crop loss display element based on the crop loss metric and controls a display device to display the first crop loss display element relative to a target loss range indicator indicative of a target loss range. A historic crop loss display generator generates a historic crop loss display element, based on previously generated crop loss metrics, and controls the display device to display the historic crop loss display element relative to the target loss indicator and relative to the first crop loss display element.

BRIEF DESCRIPTION OF THE DRAWINGS

FIGS. 4B-1-B-3 show examples of user interface displays where an instantaneous grain loss is above an expected target range.

FIGS. 4C-1-C-3 show examples of user interface displays where an instantaneous grain loss is within an expected target range.

FIGS. 4D-1-D-3 show examples of user interface displays where an instantaneous grain loss is below an expected target range.

FIGS. 4E-1-E2 and FIGS. 4F-1-F-2 show examples of shifting user interface displays.

DETAILED DESCRIPTION

Figure 1:
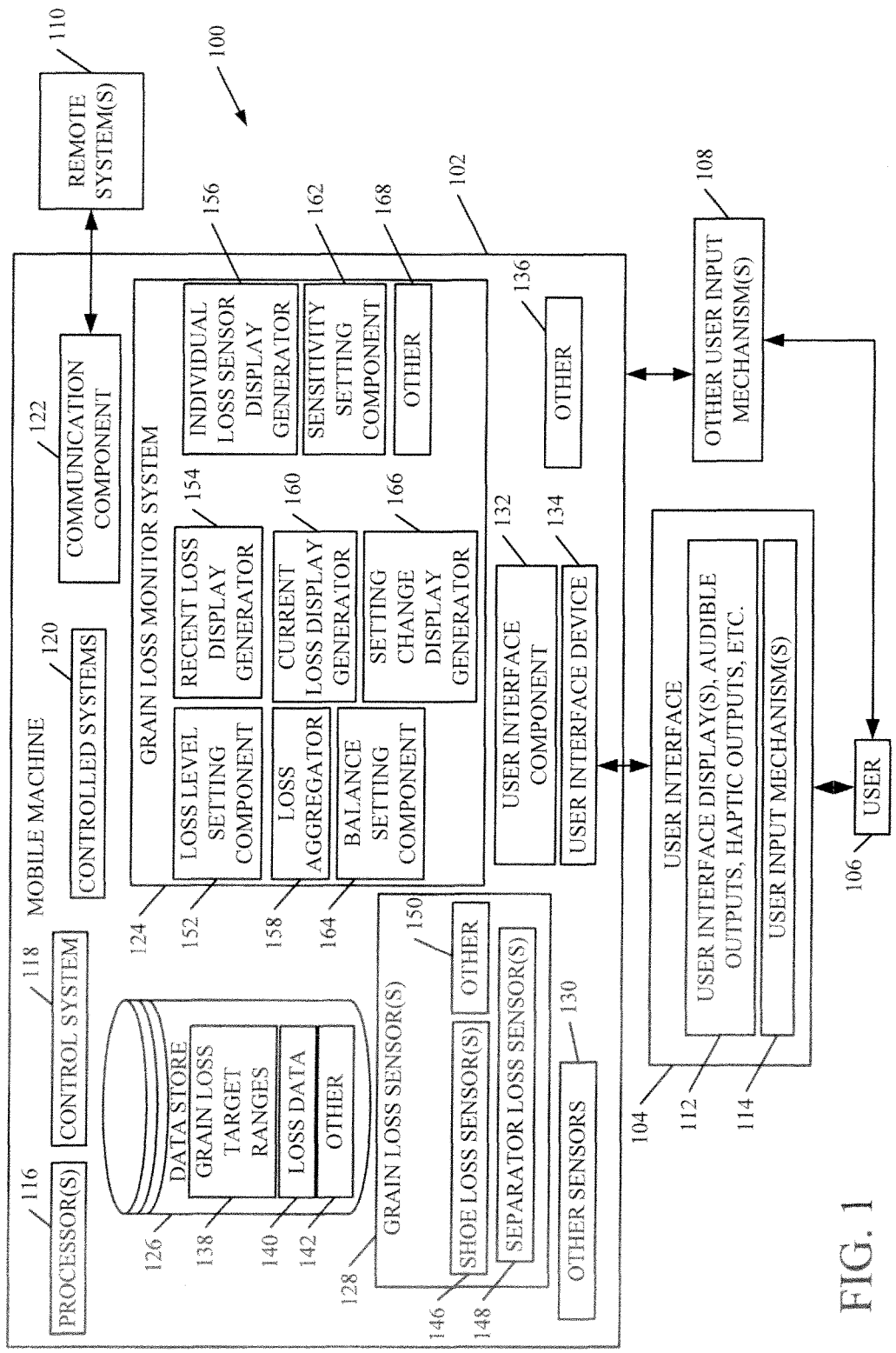
FIG. 1 is a block diagram of one example of a crop loss monitoring and surfacing architecture that monitors crop loss and surfaces it for user interaction.

FIG. 1 is a block diagram of one example of a crop loss monitoring and surfacing architecture 100. Architecture 100 shows mobile machine 102 generating user interfaces 104 for interaction by user (or operator) 106. User interfaces 104 can include user interface displays, audible outputs, haptic outputs, etc., all generally designated by 112. It can also include a set of user input mechanisms 114. User 106 illustratively interacts with user input mechanisms 114 in order to control and manipulate various portions of mobile machine 102. Architecture 100 also shows that mobile machine 102 can be connected to various remote systems 110. User 106 can also use other user input mechanisms 108 to interact with mobile machine 102.

User input mechanisms 114 can be displayed on user interface displays 112. Therefore, they can be touch sensitive display elements, icons, links, etc. Other user input mechanisms 108 can be a whole host of user input mechanisms that can be used to control machine 102. These can include such things as switches, levers, push buttons, keypads, pedals, joysticks, etc.

In the example described herein, mobile machine 102 may be an agricultural harvesting machine, or it can be another type of machine (such as a tractor) that pulls an external harvesting machine. In the latter case, some or all of the components shown in mobile device 102 may be on the external machine. However, the present description will proceed with respect to machine 102 being the harvester, itself. Also, it will be noted that the present discussion will proceed with respect to mobile machine 102 harvesting grain, but it could be harvesting other crops as well, such as sugarcane, cotton, sugar beets, etc.

In the example shown in FIG. 1, mobile machine 102 illustratively (and by way of example only) includes one or more processors 116, control system 118, controlled systems 120 and communication component 122. It can also include grain loss monitor system 124, data store 126, grain loss sensors 128, and one or more other sensors 130. Further it can include user interface component 132, user interface device 134, and it can include a wide variety of other items 136. Data store 126 can store grain loss target ranges 138, historic loss data 140, and a wide variety of other data 142. Grain loss sensors 128 can illustratively include one or more shoe loss sensors 146, one or more separator loss sensors 148, and it can include other grain loss sensors 150.

Grain loss monitor system 124 illustratively includes loss level setting component 152, recent loss display generator 154, individual loss sensor display generator 156, loss aggregator 158, current loss display generator 160, sensitivity setting 162, balance setting component 164, settings change display generator 166, and it can include other items 168. Before describing architecture 100, and its operation, in more detail, a brief overview of some of the components will first be provided.

Control system 118 illustratively receives inputs from various sensors 128-130. Sensors 130 can sense a wide variety of variables and provide sensor signals to system 118. System 118 illustratively generates control signals that are provided to control the controlled systems 120. Controlled systems 120 can be electrical systems, mechanical systems, hydraulic systems, pneumatic systems, air-over-hydraulic systems, or other systems. These systems can perform harvesting functions and a wide variety of other functions.

Grain loss sensors 128 can provide sensor signals not only to control system 118, but to grain loss monitor system 124. System 124 generates a grain loss display showing current, and recent, grain loss.

Loss aggregator 158 can aggregate the signals from the various grain loss sensors 128 to obtain an aggregate loss metric value that indicates an aggregate grain loss. Recent loss display generator 154 and current loss display generator 160 generate a display showing a current grain loss level that is occurring in machine 102, as well as a recent history of grain loss that occurred in machine 102.

Sensitivity setting component 162 can be actuated by user 106 to change the sensitivity of the displayed grain loss (or its resolution). Balance setting component 164 can be actuated to change how loss aggregator 158 treats the various sensor signals in generating the aggregate loss metric. For instance, it can change an affect that the sensor signal from each of the different grain loss sensors 128 has on the aggregate, or overall grain loss metric.

Loss level setting component 152 illustratively generates a user experience that allows the user to set a current grain loss level as a desired grain loss level. It resets a target grain loss range 138 around the current grain loss level on a visual display.

Individual loss sensor display generator 156 allows user 106 to view the grain loss sensed by the individual grain loss sensors 128. This can be displayed on a single display or multiple different displays.

Settings change display generator 166 illustratively generates visual indicia that indicate when, on the grain loss display, settings were changed on mobile machine 102. For instance, where mobile machine 102 is a combine, the visual indicia indicating a settings change may indicate a point at which the concave clearance or threshing speed were changed, or where the cleaning fan speed, chaffer position, or sieve positions were changed, among other things.

Grain loss monitor system 124 can control user interface component 132 to generate the grain loss display using user interfaces 104 on user interface device 134. A variety of different examples of these user interfaces are described in greater detail below.

Figure 2:
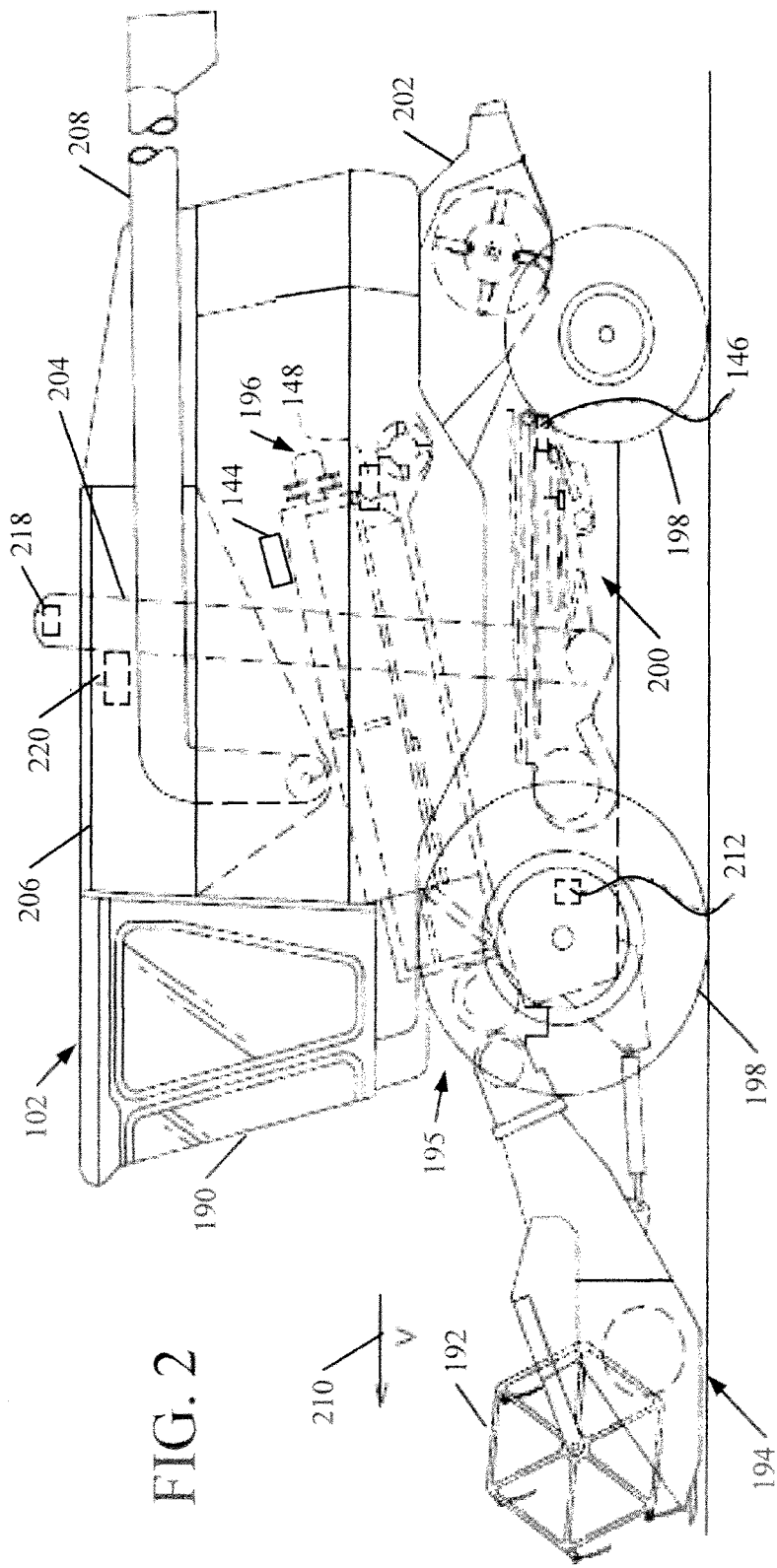
FIG. 2 is a pictorial illustration of an implementation of the architecture illustrated in FIG. 1, deployed on a combine.

FIG. 2 shows one example of a pictorial illustration in which mobile machine 102 is a combine. FIG. 2 also shows a number of the items illustrated in FIG. 1, deployed on the combine. It can be seen in FIG. 2 that combine 102 illustratively includes an operator compartment 190, a header 192, a cutter generally indicated at 194, a thresher generally indicated at 195, a set of ground engaging wheels 198, a separator 200, a spreader 202, an elevator 204, a clean grain tank indicated by arrow 206 and a spout 208. In operation, combine 102 illustratively travels in the direction generally indicated by arrow 210. Header 192 engages the product being harvested and gathers it toward cutter 194. After it is cut, it is moved toward thresher 195 where it is threshed, and then moved to separator 196. The grain falls to cleaning shoe 200 and the clean grain is moved by elevator 204 into clean grain tank 206. Tailings can be passed back to thresher 195 where they are re-threshed. Material other than grain (such as stalks, husks, etc.) can be chopped and removed from machine 102 by spreader 202.

FIG. 2 also shows that, in one example, combine 102 includes a ground speed sensor 212, one or more cleaning shoe loss sensors 146, one or more separator loss sensors 148, a clean grain camera 220 and a tailings camera 144. Ground speed sensor 212 illustratively senses the travel speed of combine 102 over the ground. This can be done by sensing the speed of rotation of the wheels, the drive shaft, the axel, or other components. The travel speed can also be sensed by a positioning system, such as a global position system (GPS), a dead reckoning system, a LORAN system, or a wide variety of other systems or sensors that provide an indication of travel speed.

Cleaning shoe loss sensors 146 illustratively provide an output signal indicative of the quantity of grain loss by both the right and left cleaning shoes. In one example, sensors 146 are strike sensors which count grain strikes per unit of time (or per distance of travel) to provide an indication of the cleaning shoe grain loss. The strike sensors for the right and left cleaning shoes can provide individual signals, or a combined or aggregate signal. It will be noted that sensors 146 can comprise only a single sensor as well, instead of separate sensors for each shoe.

Separator loss sensors 148 provide a signal indicative of grain loss in the left and right separators 196. The sensors associated with the left and right separators 196 can provide separate grain loss signals, or a combined or aggregate signal. This can be done using a wide variety of different types of sensors as well. It will be noted that sensors 148 can comprise only a single sensor as well, instead of separate left and right sensors.

Tailings camera 144 illustratively generates a video image of the tailings that are being passed back to the thresher for re-threshing. Clean grain camera 220 illustratively provides a video image indicative of the quality of the grain being deposited in clean grain tank 206. Either or both of cameras 220 and 144 can provide the images to a video analysis system that can analyze the video images to generate various different metrics. For instance, clean grain camera 220 can provide its signal to a video analysis system that outputs an indication of a quantity of cracked grain, whole grain, etc., that is entering the clean grain tank. Tailings camera 144 can illustratively provide its video image signal to a video analysis system that identifies a tailings volume of the tailings. All of these are described for the sake of example only.

Yield monitor 218 can be a sensor that senses yield. In one example, it can sense mass flow through elevator 204. It can provide an output signal indicative of this, to indicate the particular yield. This can be measured in bushels per hour, bushels per hectare, tons per hour or in other units.

Figure 3A:
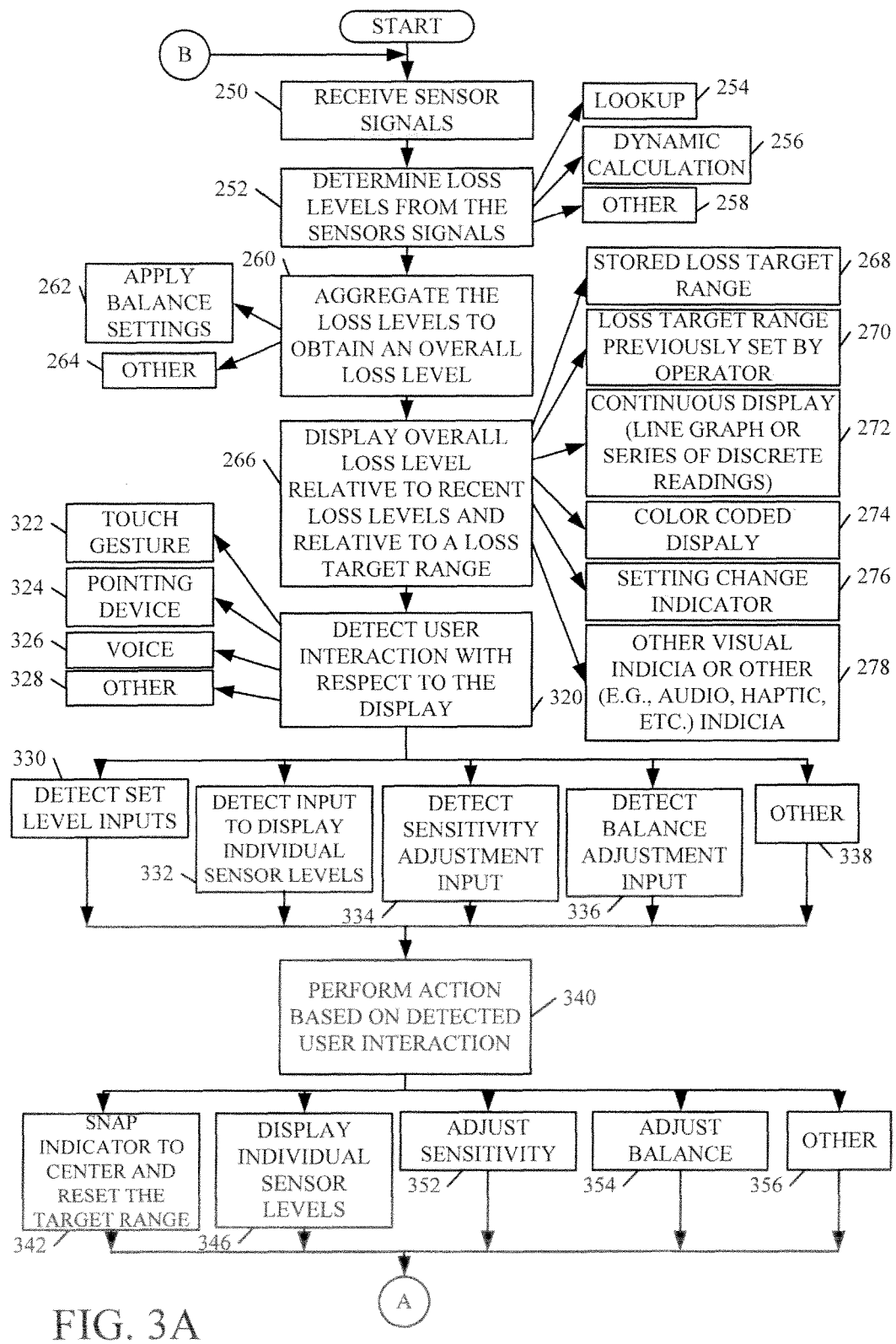
FIGS. 3A and 3B (collectively referred to as FIG. 3) show a flow diagram illustrating one example of the operation of the architecture shown in FIG. 1.
Figure 3B:
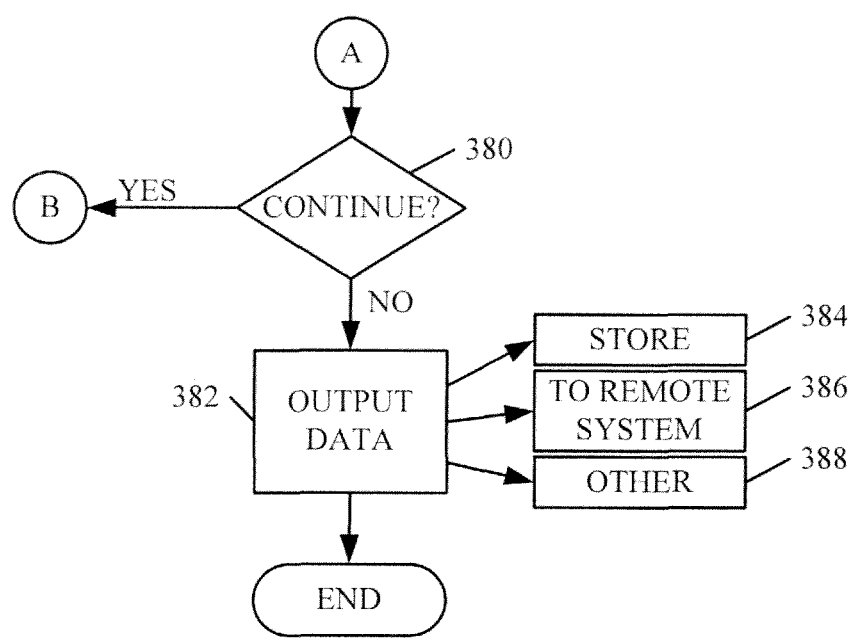

FIGS. 3A and 3B (collectively FIG. 3) show a flow diagram illustrating one example of the operation of mobile machine 102 and grain loss monitor system 124 in monitoring grain loss, and surfacing that information for interaction by user 106. FIGS. 4A-4H show various examples of user interface displays that can be generated. FIGS. 1-4H will now be described in conjunction with one another.

Figure 4A:
FIGS. 4A and A-1 show examples of user interface displays.
Figures 1, 4A:
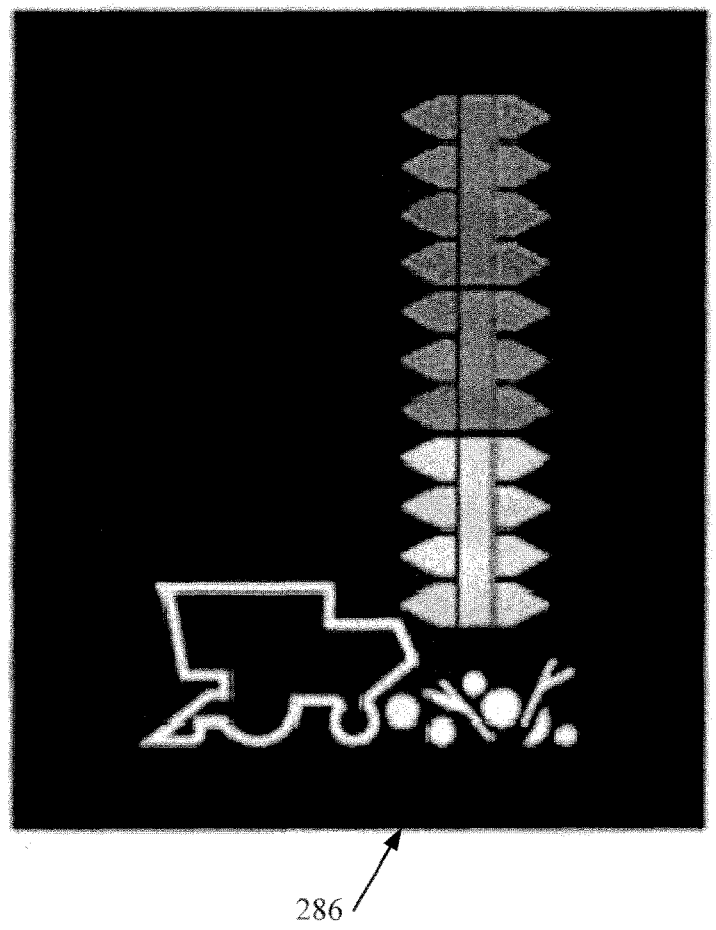
Figures 1, 4B:
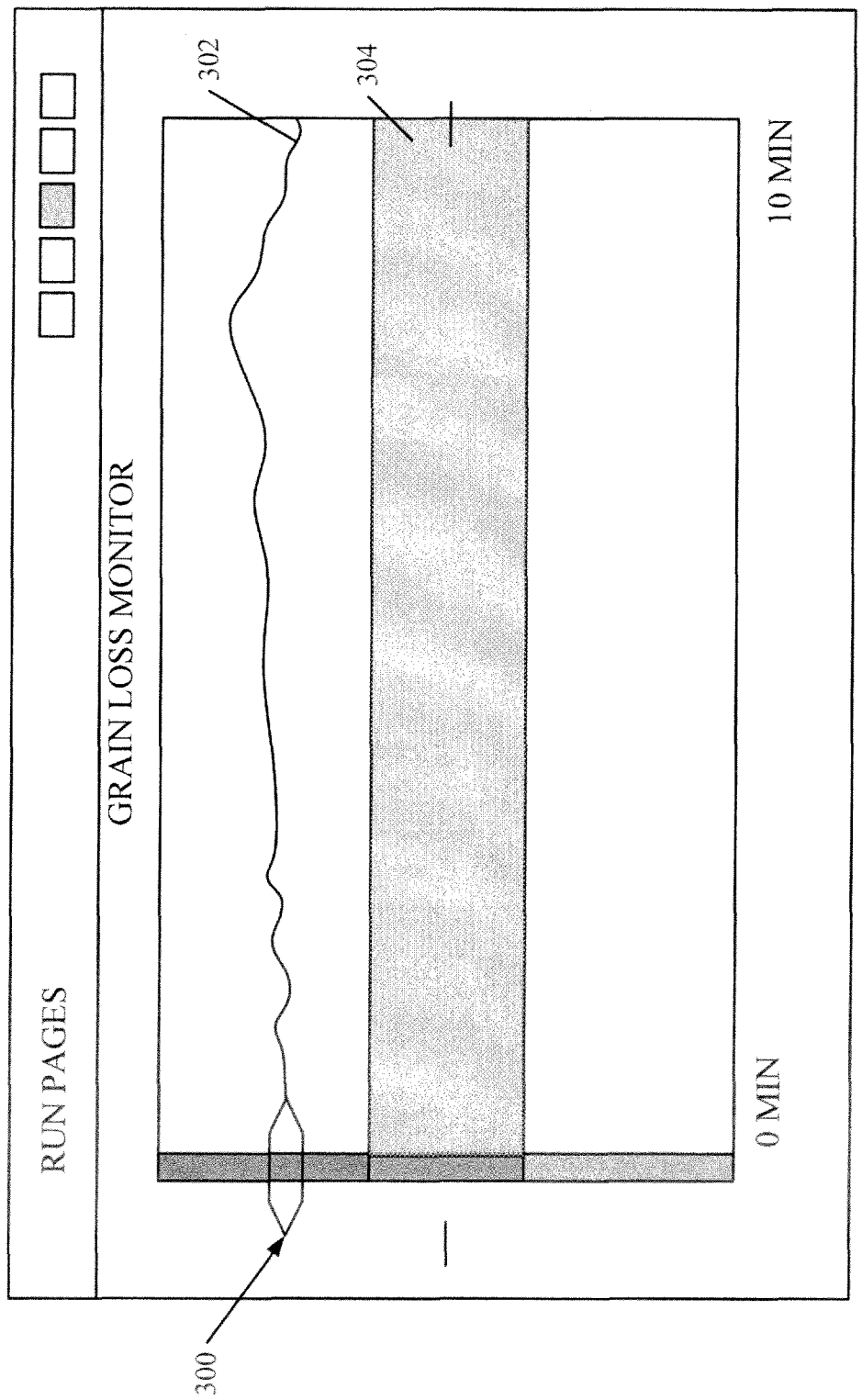
Figures 2, 4B:
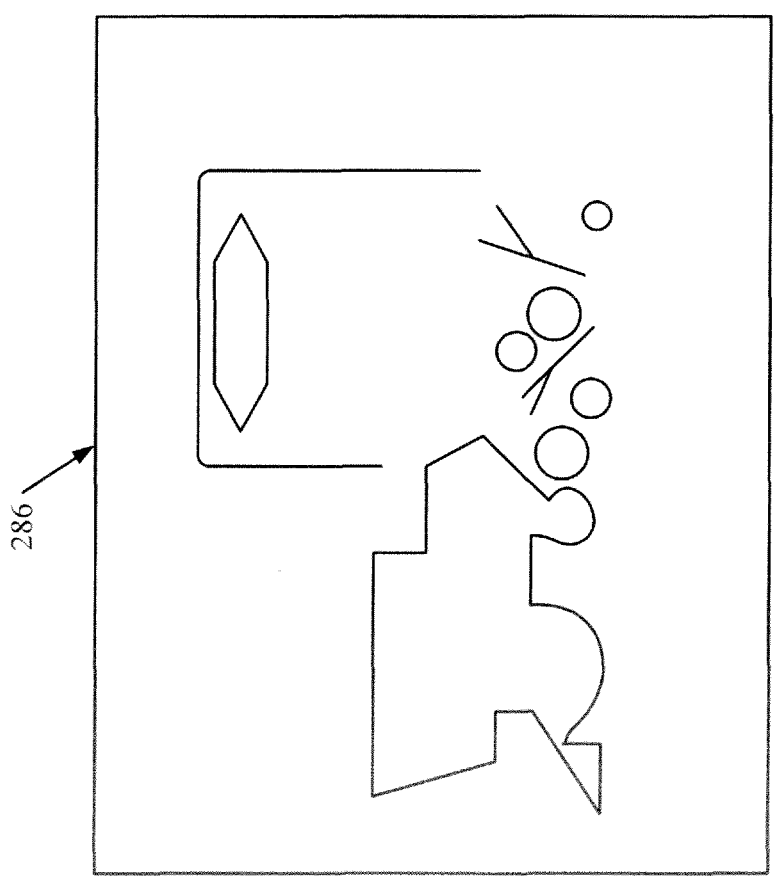
Figures 3, 4B:
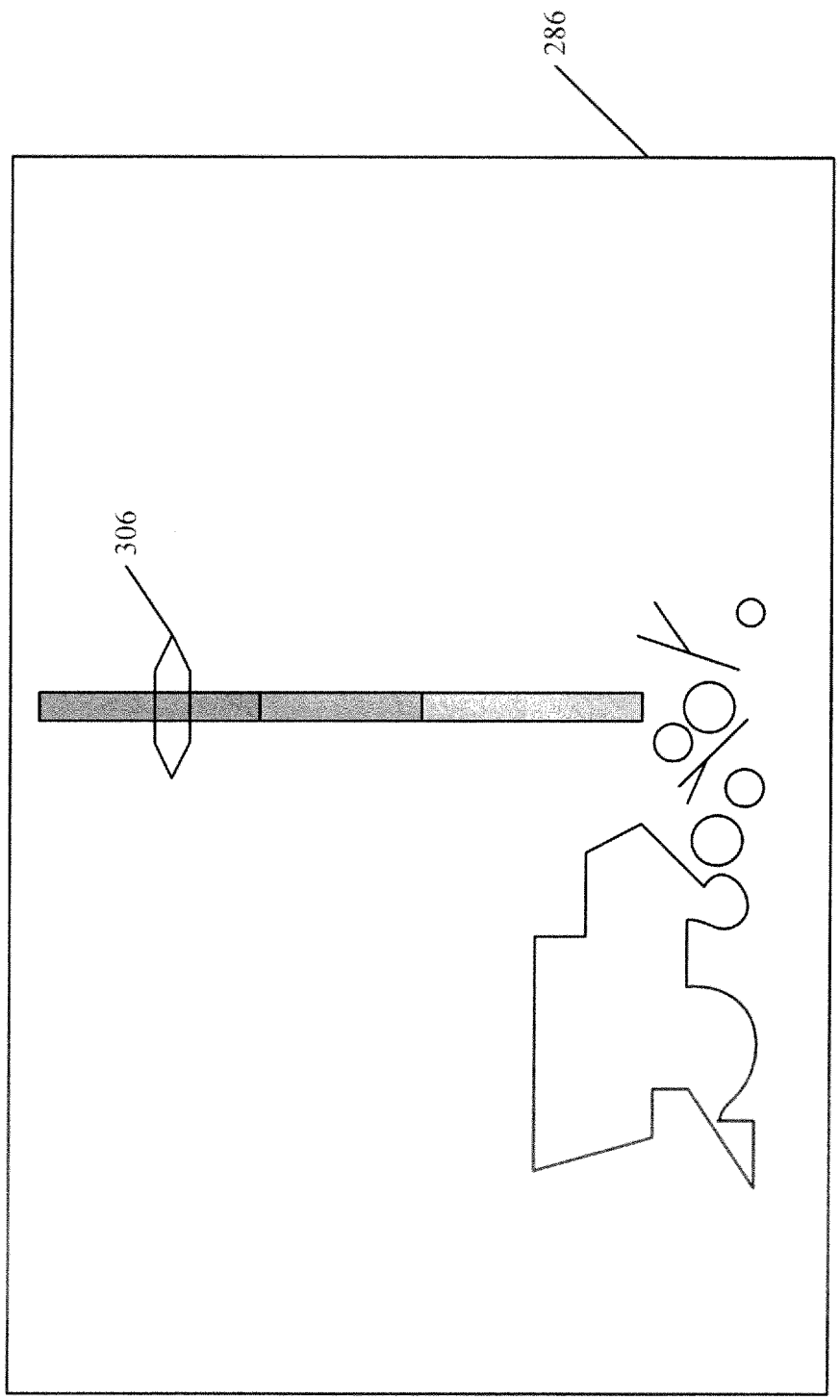

In the example shown in FIG. 3, it is assumed that mobile machine 102 is operating and is conducting a harvesting operation. It will be assumed for the sake of the present discussion that mobile machine 102 is harvesting grain. However, it will be appreciated that the same discussion could be had with respect to harvesting other items where loss is detected.

Grain loss monitor system 124 first receives the sensor signals from grain loss sensors 128. This is indicated by block 250 in FIG. 3. In one example, the sensors are provided to a sensor conditioning system that conditions the sensor signals, such as by performing linearization, calibration, amplification, etc. Grain loss monitor system 124 then determines a current (or sensed) loss level from the sensor signals. This is indicated by block 252 in FIG. 3. In one example, grain loss monitor system 124 performs a table lookup based on the level of the sensor signals received. The table lookup identifies a grain loss level corresponding to each of the sensor signals, given their present level. Performing a lookup is indicated by block 254. In another example, system 124 performs a dynamic calculation that calculates the grain loss level, given the sensor signals. This can also consider other sensed variables as well. Performing a dynamic calculation is indicated by block 256. Determining the grain loss levels from the sensor signals can be done in other ways as well, and this is indicated by block 258.

Loss aggregator 158 then aggregates the loss corresponding to each of the different sensor signals to obtain an overall loss level that represents an aggregate loss sensed by the various sensors. This is indicated by block 260. In one example, loss aggregator 158 generates the overall loss level by applying balance settings that are set using balance setting component 164. For instance, aggregating the loss levels can be done by simply adding the loss levels corresponding to each of the sensor signals together, by combining them in a weighted fashion or in other ways. They may be combined in a weighted fashion, for instance, because it may be that the loss level identified based on the separate loss sensor 148 (for instance) is less reliable than that from the other sensors. Therefore, the proportion of the overall loss level attributed by loss aggregator 158 to the loss sensed by sensor 148 may be lower than that for the other grain loss sensors 128. In one example, as described in greater detail below, balance setting component 164 generates a user interface display with user input mechanisms that can be actuated in order to adjust the balance among the various grain loss sensors 128 (e.g., it allows the user to change the amount of the overall loss level that is contributed by each of the different types of grain loss sensors to the overall loss generated by aggregator 158). Applying the balance settings to obtain the overall loss level is indicated by block 262. Obtaining the overall loss level in other ways is indicated by block 264.

Current loss display generator 160 then generates a display of the current overall loss level. Recent loss display generator 154 generates a display indicative of historic loss levels for an immediate history. For instance, it may generate a display indicative of the overall loss level sensed for the last 10 minutes, or for the last 20 meters of distance traveled by mobile machine 102, etc. Thus, current loss display generator 160 and recent loss display generator 154 combine to display the current overall loss level relative to recent loss levels and relative to a loss target range. This is indicated by block 266 in FIG. 3.

The target range can be a pre-determined, stored target range or it can be one set by the operator or user 106. As is described in greater detail below, loss level setting component 152 illustratively generates a user interface display, with user input mechanisms that allow user 106 to set the target range for the overall loss. Therefore, the instantaneous, current loss, and the recent history of the overall loss can be displayed relative to the target range. Displaying the instantaneous, current overall loss level relative to a stored loss target range is indicated by block 268. Displaying it relative to a loss target range that was set by the operator is indicated by block 270. The loss level can be displayed as a continuous display, such as a line or trace graph or a series of discrete readings displayed in close proximity relative to one another. This is indicated by block 272. The overall loss level can have color-coded portions indicating whether it is above, within, or below the target range. This is indicated by block 274. It can be displayed along with settings change indicators that identify, on the continuous display, when harvester settings were changed. This will allow the operator to see what affect the settings change has had on the overall loss level detected. Displaying the settings change indicator is indicated by block 276 in FIG. 3. The display can include other visual indicia or other indicia (such as audio outputs, haptic outputs, etc.). This is indicated by block 278.

Before proceeding with a further description of the operation of grain loss monitor system 124, a number of examples of user interface displays will first be discussed. It will first be noted that the user interface displays can be generated on a wide variety of different types of devices. Some of those are described below with respect to FIGS. 4A-4H and 6-9. Those illustrated are examples only.

FIG. 4A shows one example of a user interface display device 280. Display device 280 is shown as a quarter video graphics array or (QVGA) display device. In the example shown in FIG. 4A, it has a first portion 282 that displays a set of fixed display elements. It also has a second portion 284 that shows a set of reconfigurable display elements (although in FIG. 4A, portion 284 is blank). Of the fixed display elements shown in portion 282, a grain loss indicator 286 is illustratively included. It can be seen that grain loss indicator 286 illustratively has a level identifier portion 288 that includes three different levels represented by three different display elements 290, 292 and 294. When display element 290 is illuminated, this indicates that the grain loss is above the target range. When display element 292 is illuminated, this indicates that the grain loss is within the target range, and when display element 294 is illuminated, this indicates that the sensed grain loss is below the target range. In one example, each of the display elements 290-294 are color-coded as well.

FIG. 4A-1 shows another example of grain loss indicator 286. It is similar to that shown in FIG. 4A, except that each of the ranges (above, within, or below the target range) is represented by multiple different display elements. Therefore, the user can easily determine whether the detected grain loss is well outside of the target range, is near the edge of the target range, etc.

When the user actuates one of the fixed display elements on portion 282, the reconfigurable display portion 284 can be used to display more detailed information corresponding to the actuated element. FIGS. 4B-1 to 4B-3 show a set of user interface displays that can be displayed by grain loss monitor system 124 to show that the current detected grain loss is above the target range. FIG. 4B-1 shows one example of a display that can be shown on the reconfigurable display portion 284. The left hand side of the display shown in FIG. 4B-1 shows an instantaneous grain loss indicator 300 and a continuous or historic grain loss indicator 302. FIG. 4B-1 also shows one example of a target range indicator 304. The target range indicator 304 is shaded, color-coded, or otherwise visually distinguished from a remainder of the display shown in FIG. 4B-1.

In the example shown in FIG. 4B-1, instantaneous display indicator 300 is displayed to indicate that the currently detected grain loss is above the target range, because indicator 300 is displayed above target range indicator 304. The continuous indicator 302 shows detected grain loss over the previous 10 minutes. This can be continuously detected, or detected at discrete moments in time. Thus, continuous indicator 302 can be a line or trace (as shown in FIG. 4B-1) or it can be a set of discrete points displayed in close proximity relative to one another. In the example shown in FIG. 4B-1, the instantaneous grain loss, as well as the grain loss detected over the previous 10 minutes, are all above the desired target range illustrated by indicator 304.

FIG. 4B-2 shows one example of the fixed grain loss indicator 286 illustrating that the instantaneous grain loss is above the expected target range. FIG. 4B-3 shows another example of the grain loss indicator 286 with an instantaneous loss element 306 indicating that the currently detected grain loss is above the target range.

Figures 1, 4C:
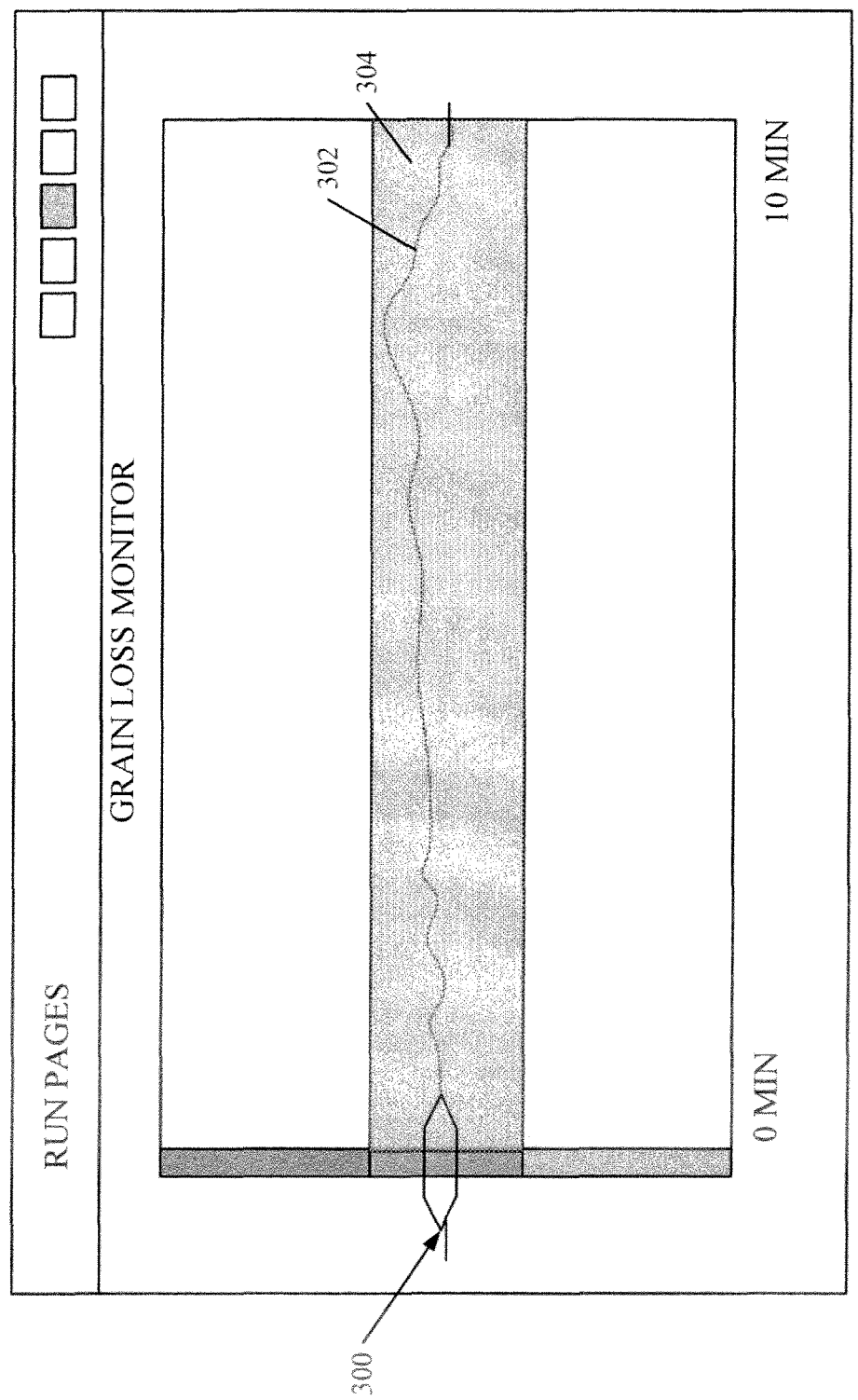
Figures 2, 4C:
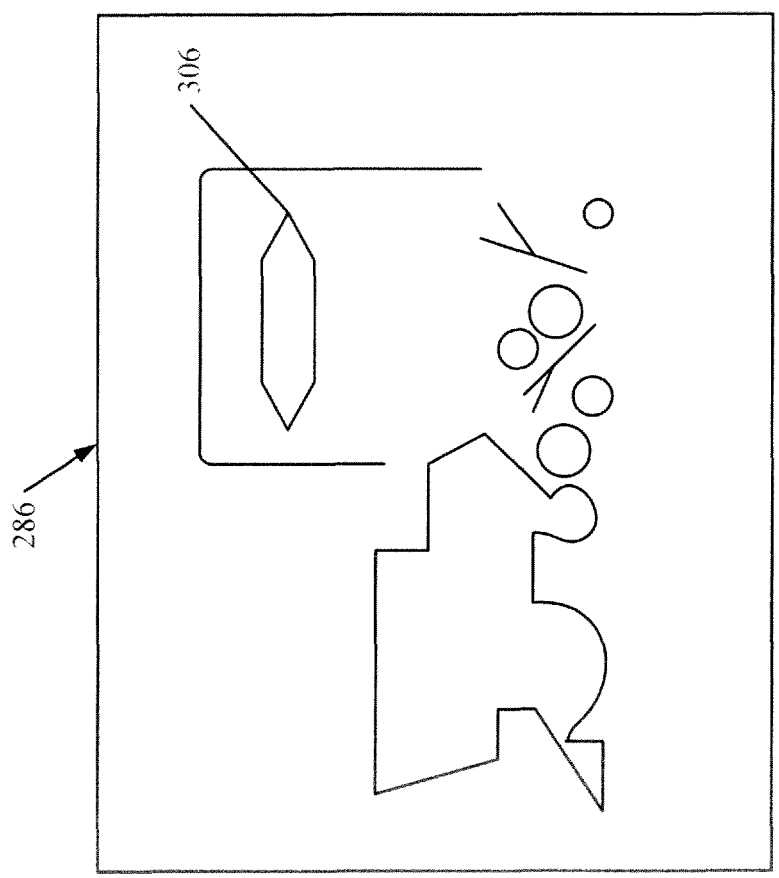
Figures 3, 4C:
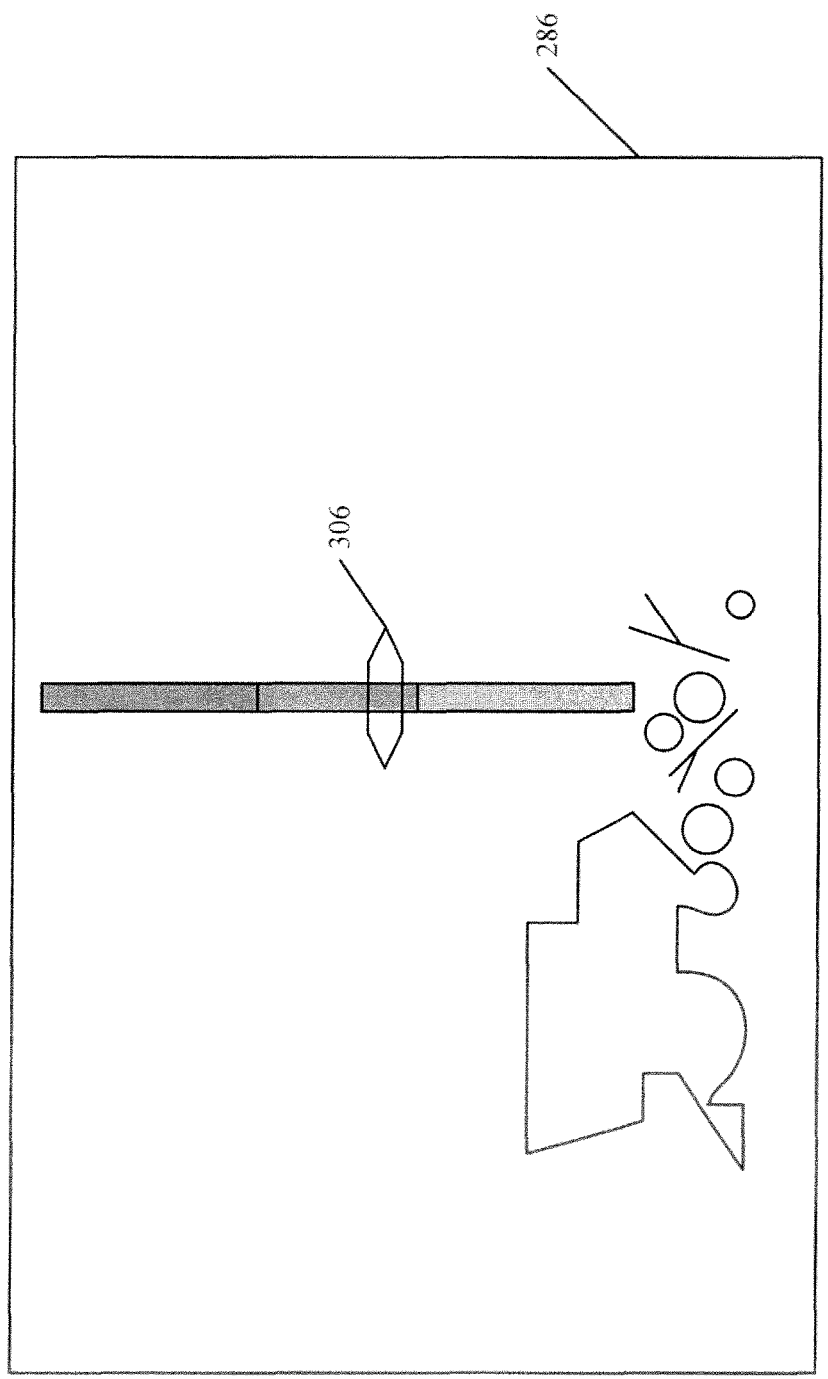

FIGS. 4C-1 to 4C-3 are similar to FIGS. 4B-1 to 4B-3 except that FIGS. 4C-1 to 4C-3 show that the instantaneous, and historic, grain loss is now within the target range represented by indicator 304. FIGS. 4D-1 to 4D-3 are similar to FIGS. 4B-1 to 4B-3 and 4C-1 to 4C-3 described above, except that FIGS. 4D-1 to 4D-3 show that the instantaneous grain loss, as well as the historic grain loss over the last 10 minutes, is at or below the target range represented by indicator 304.

Referring again to the flow diagram of FIG. 3, once display generators 150 and 154 display an indication of the currently detected grain loss, and the recent history of the detected grain loss, the user can illustratively interact with any of user input mechanisms 108 and 114, to modify the display. Detecting user interaction with respect to the display is indicated by block 320 in the flow diagram of FIG. 3. The user can interact with the display using a touch gesture 322 where the display is displayed on a touch sensitive display device. The user can interact with the display using a pointing device (such as a mouse, a joystick, a trackball, etc.). This is indicated by block 324. In one example, the user can also interact with the display by providing a voice user input as indicated by block 326, or in other ways as indicated by block 328.

In addition, the user interactions can serve a variety of different purposes. For instance, the user interaction can be a level setting user interaction provided to loss level setting component 152 in order to reset the target range represented by indicator 304 for the detected grain loss level. This may occur in a variety of different ways. For example, the machine operator 106 may observe that the current grain loss is at an acceptable level, and that he or she wishes to keep the grain loss at approximately that same level. User 106 can provide an input to loss level setting component 152 indicating that he or she would like to set the loss level so that the target range is approximately centered around the currently detected loss level. The user can do this, for instance, by pressing a button, or using any of the other mechanisms described above. Detecting a set level input to reset the target range is indicated by block 330.

The user input can also be a user input that configures the display to show individual loss levels detected by the individual grain loss sensors 128. In that case, individual loss sensor display generator 156 can generate such a display. Detecting a user input to display the individual sensor levels is indicated by block 332.

The user input can also be provided to sensitivity setting component 162. It can be used to reset the sensitivity of the display (or the resolution of the display). Detecting a sensitivity adjustment input is indicated by block 334.

The input can be provided to balance setting component 164. It can be used to reset the balance of the individual grain loss sensors 128 in determining the overall loss level. For instance, as described above, the user may wish to have aggregator 158 attribute more weight to one of the different grain loss sensors 128 than to others, in determining the overall grain loss level. Detecting a balance adjustment input is indicated by block 336. Of course, the user interactions can take a wide variety of other forms as well. This is indicated by block 338.

Once grain loss monitor system 124 detects user interaction relative to the display, it can perform an action based on the detected user interaction. This is indicated by block 340 in FIG. 3. For example, when a level setting input is detected, loss level setting component 152 controls user interface component 152 to display the user interface display so that the instantaneous grain loss level indicator 300 (shown in FIGS. 4B-1 to 4D-3) appears to snap to the center of the vertical axis in the target range indicated by indicator 304. The historical grain loss indicator 302 also visually displaces in the same direction (either up or down on the display) by an equal amount as indicator 300, giving the impression that the entire line has shifted vertically by an amount corresponding to that by which the instantaneous indicator 300 shifted. Snapping the instantaneous indicator 300 and the historical indicator 302 to the center of the target range 304 is indicated by block 342 in the flow diagram of FIG. 3. FIGS. 4E-1 to 4F-2 illustrate one example of this.

FIG. 4E-1 shows a similar display to that illustrated in FIG. 4B-1, in which the instantaneous grain loss indicator 300 is above the target range represented by indicator 304, as is the historical grain loss indicator 302. However, a set of user input mechanisms 344 is also displayed. When the user actuates one of the user input mechanisms (such as the check mark 345) this causes both the instantaneous loss indicator 300 and the historical loss indicator 302 to displace vertically on the user interface display so that the instantaneous loss indicator 300 is at a center of the target range indicator 304. Thus, when the user actuates the check mark user input mechanism 345, the display of FIG. 4E-1 snaps to that shown in FIG. 4E-2.

Figures 1, 4D:
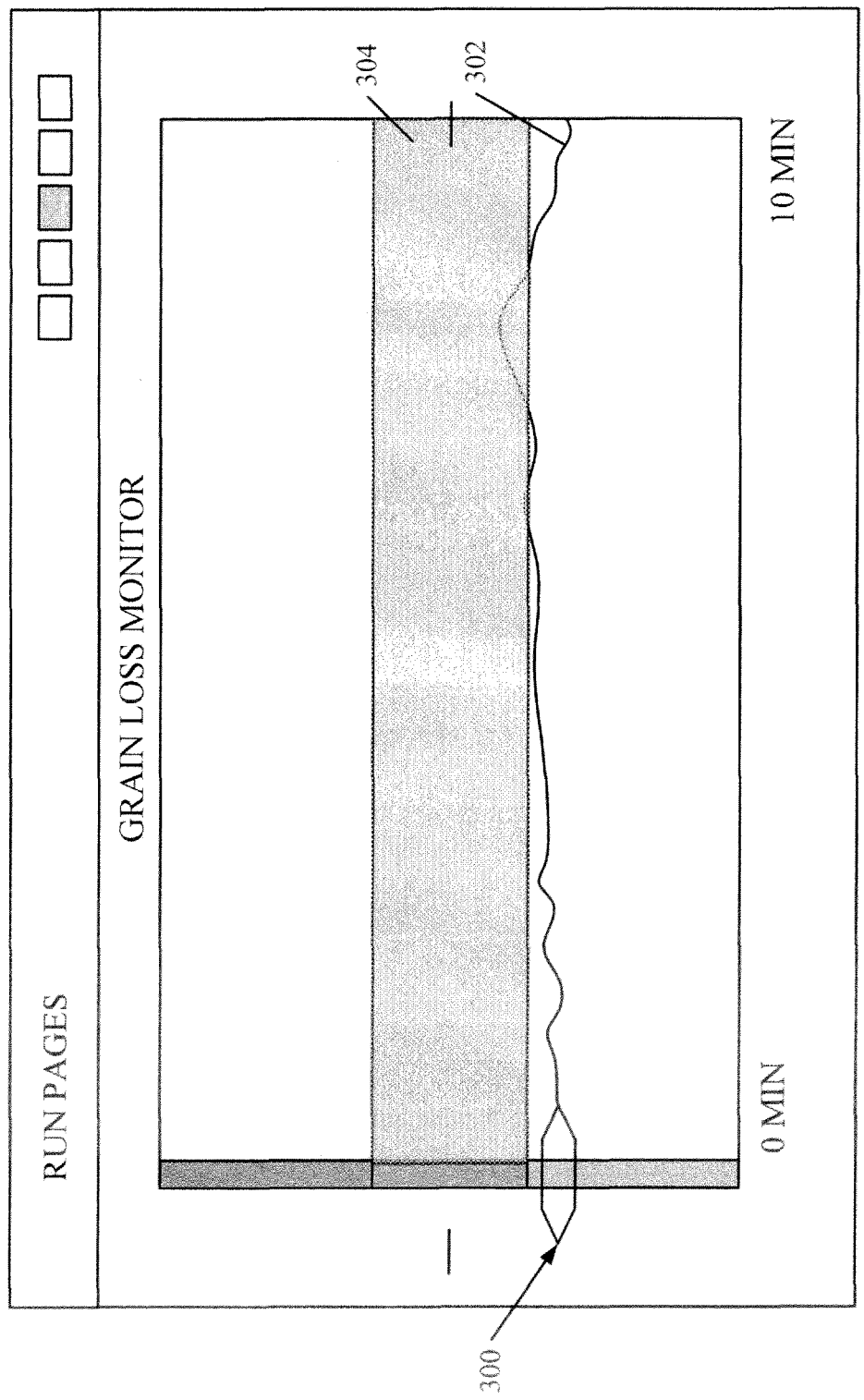
Figures 2, 4D:
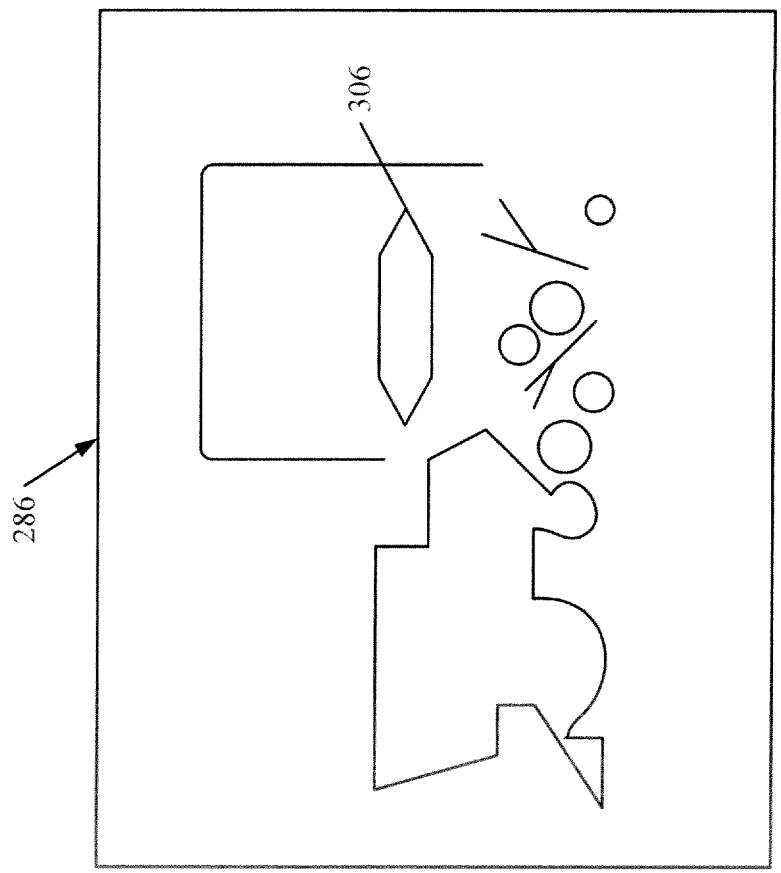
Figures 3, 4D:
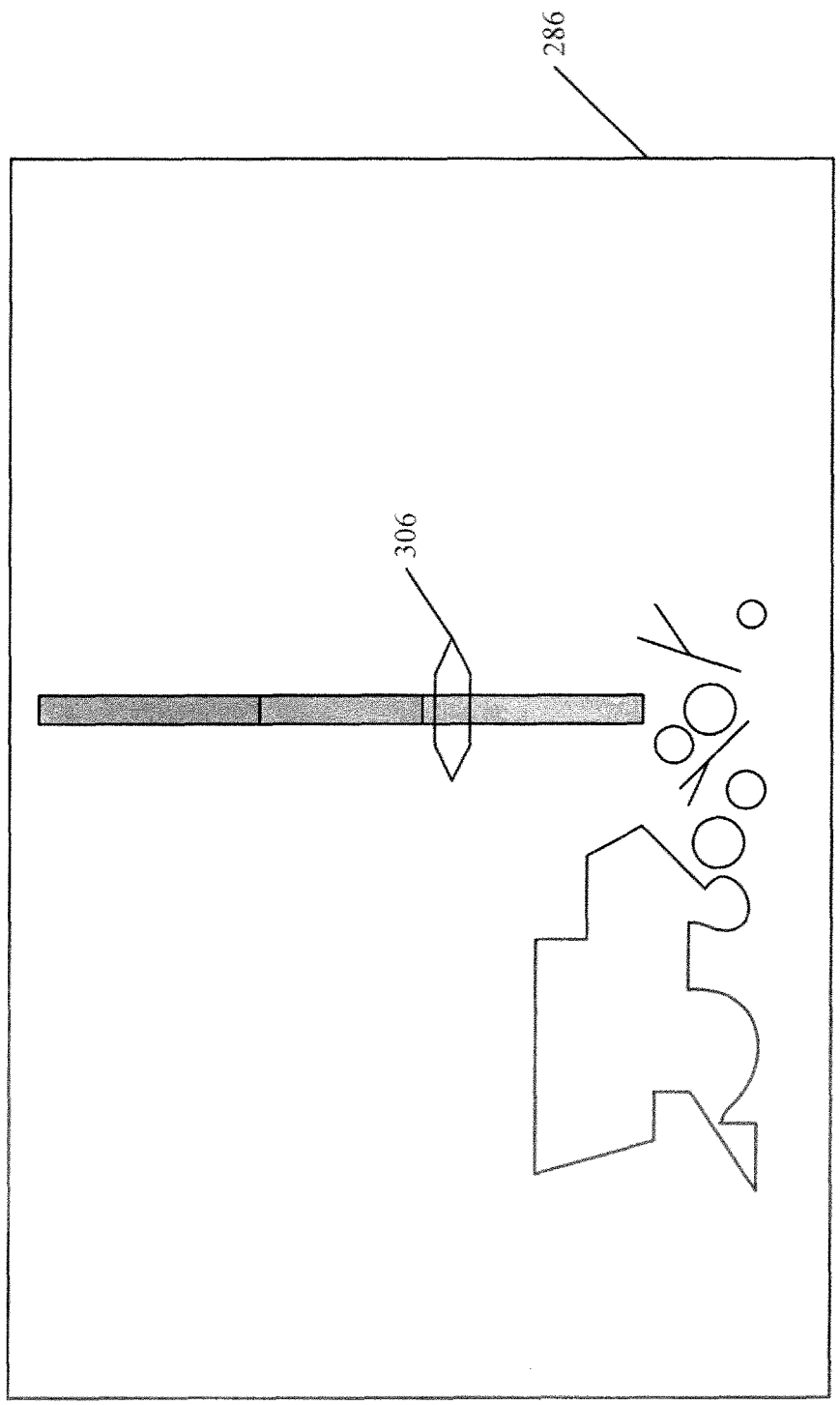

FIG. 4F-1 shows a similar display to that shown in FIG. 4D-1, in which the instantaneous loss indicator 300, as well as a majority of the historical loss indicator 302, are below the target range indicator 304. The same user input mechanisms 344 are displayed so that the user can adjust this. When the user actuates the check mark user input mechanism 345, the instantaneous loss indicator 300 and the historical loss indicator 302 again displace vertically so that instantaneous loss indicator 300 snaps to the center of target range indicator 304. Historical loss indicator 302 shifts vertically by the same amount so that the display is now that shown in FIG. 4F-2.

Figure 4G:
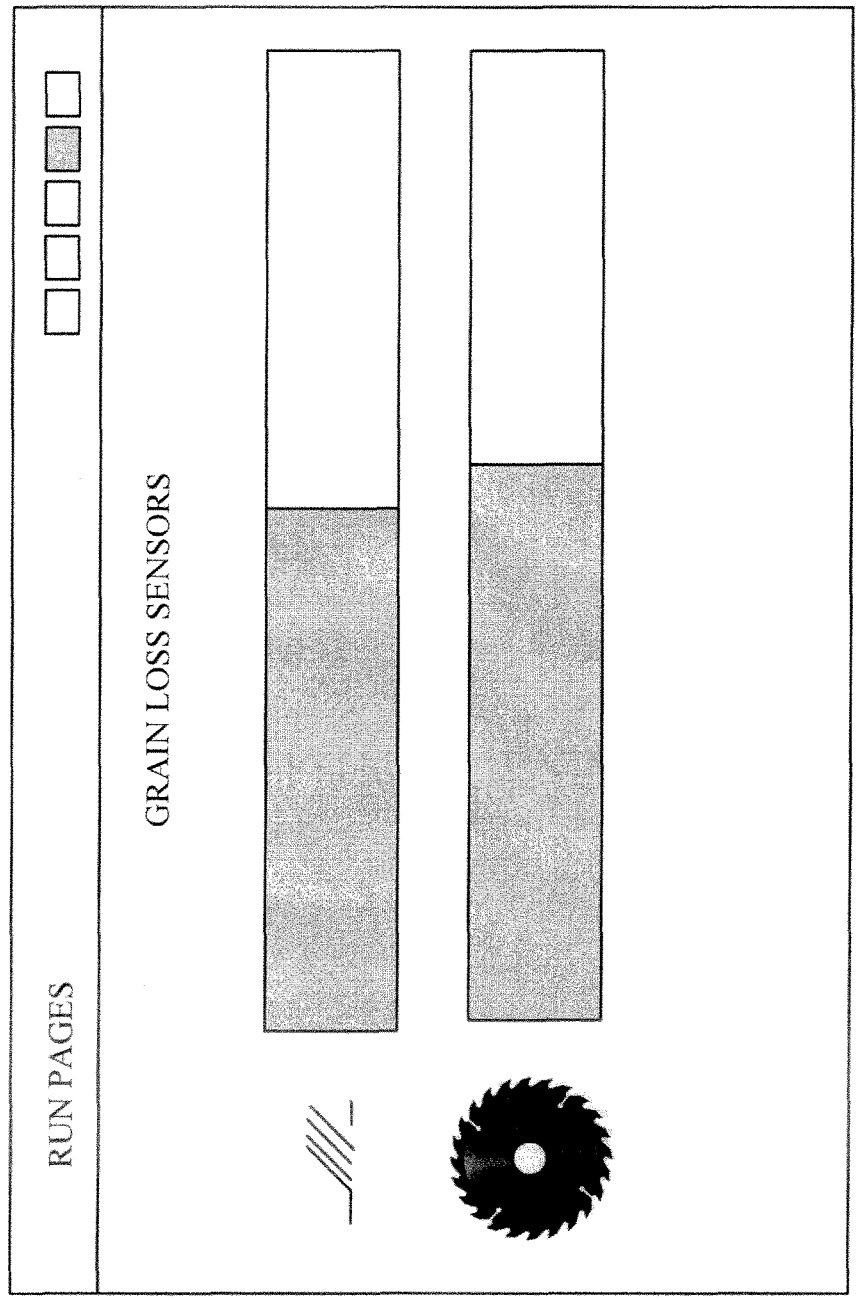
FIG. 4G shows an example of a sensor level user interface display.

Referring again to the flow diagram shown in FIG. 3, the operator can also illustratively provide an input indicating that he or she wishes to have the individual sensor levels displayed from the individual grain loss sensors 128 (or from a subset of them). This can be done by pressing a button, actuating a touch sensitive screen, etc., as described above. Individual loss sensor display generator 156 detects this interaction and generates a display showing the individual sensor levels. FIG. 4G shows one example of this.

By way of example, the user may be viewing the user interface display shown in FIG. 4C-1 or 4E-2, or any of the other user interface displays. When the user interacts with the display indicating that the user wishes to have the individual sensor levels displayed, individual loss sensor display generator 156 detects this and generates a display, such as that shown in FIG. 4G, in which the individual sensor levels are displayed. In one example, the individual grain loss sensor displays are shown to indicate a current reading relative to the full range of the sensor. This can be provided for the user's information, and it can also be used to assist in trouble shooting and making adjustments when a currently detected loss level is outside of an acceptable range. Displaying the individual sensor levels is indicated by block 346 in the flow diagram of FIG. 3.

The user input mechanisms (such as mechanisms 344 in FIG. 4E-1) may also include a sensitivity user input mechanism 350. When the user actuates this, a display can be generated in which the user can modify the sensitivity (or resolution) of the user interface display screen. This illustratively causes sensitivity setting component 162 to modify the display to adjust the vertical loss range displayed to include more or less of the overall sensor readings. This provides a higher or lower resolution display so that the user can display more fine-grained or more course-grained loss results. Adjusting the sensitivity is indicated by block 352 in the flow diagram of FIG. 3.

The user input mechanisms 344 can also include a balance adjustment user input mechanism. In that case, the user can interact with such a user input mechanism to adjust the balance on the overall grain loss that is contributed by each of the different types of grain loss sensors 128. For instance, the user can be provided with a user input mechanism that allows the user to adjust the impact of the shoe loss sensor signal versus the separator loss sensor signal on the overall loss level that is monitored and displayed by grain loss monitor system 124. Adjusting the balance is indicated by block 354 in the flow diagram of FIG. 3.

The user can interact relative to the user interface display in other ways as well, and other actions can be performed in response to that interaction. This is indicated by block 356.

Figure 4H:
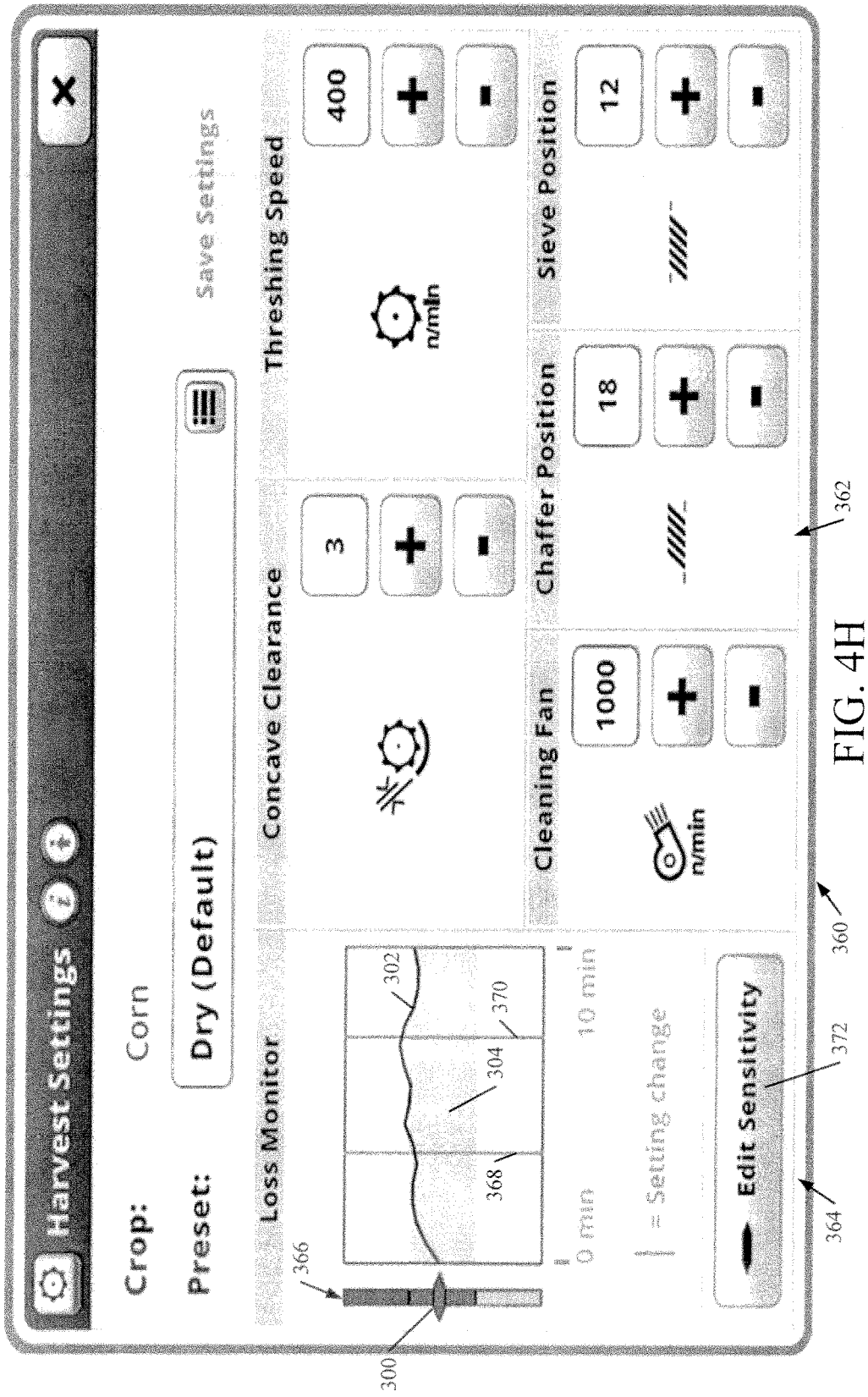
FIGS. 4H-I show examples of user interface displays.

FIG. 4H shows yet another example of how grain loss can be displayed on a different type of display device by system 124. FIG. 4H shows one example of a user interface display 360 that can be generated on a larger display device, such as on a 10-inch screen, for instance. It can be seen in display 360 that a variety of different settings can be displayed, along with user input mechanisms for adjusting those settings. This is shown generally at 362. For instance, the settings are displayed for concave clearance, threshing speed, cleaning fan speed, chaffer position and sieve position. User input mechanisms are provided for adjusting all of those settings.

The grain loss monitor system 124 illustratively generates a grain loss monitor display that is displayed in display portion 364. It can be seen that display portion 364 displays an instantaneous grain loss display 366. Display 366 includes an instantaneous loss indicator 300 that is displayed on a vertical axis (by current loss display generator 160) to indicate whether the currently detected grain loss is within, above or below a target range represented by indicator 304. In addition, the historic grain loss indicator 302 displays historic grain loss that was monitored over a previous period of time, and also displays it relative to target range indicator 304.

The display in display portion 364 also includes a set of settings change display elements 368 and 370. In the example shown in FIG. 4H, elements 368 and 370 are vertical lines that are displayed on top of the historical grain loss display indicator 302. They indicate where, within the recent history, settings were changed. In one example, when the user actuates one of the lines 368 and 370, settings change display generator 166 generates a more detailed display indicating which settings were changed, and what those changes were.

The display in display portion 364 also illustratively includes a sensitivity edit user input mechanism 372. When the user actuates mechanism 372, the user is illustratively navigated through a user experience that allows the user to increase or decrease the sensitivity (or resolution) of the grain loss display. This illustratively adjusts the vertical loss range displayed to include more or less of the overall sensor readings.

Figure 4I:
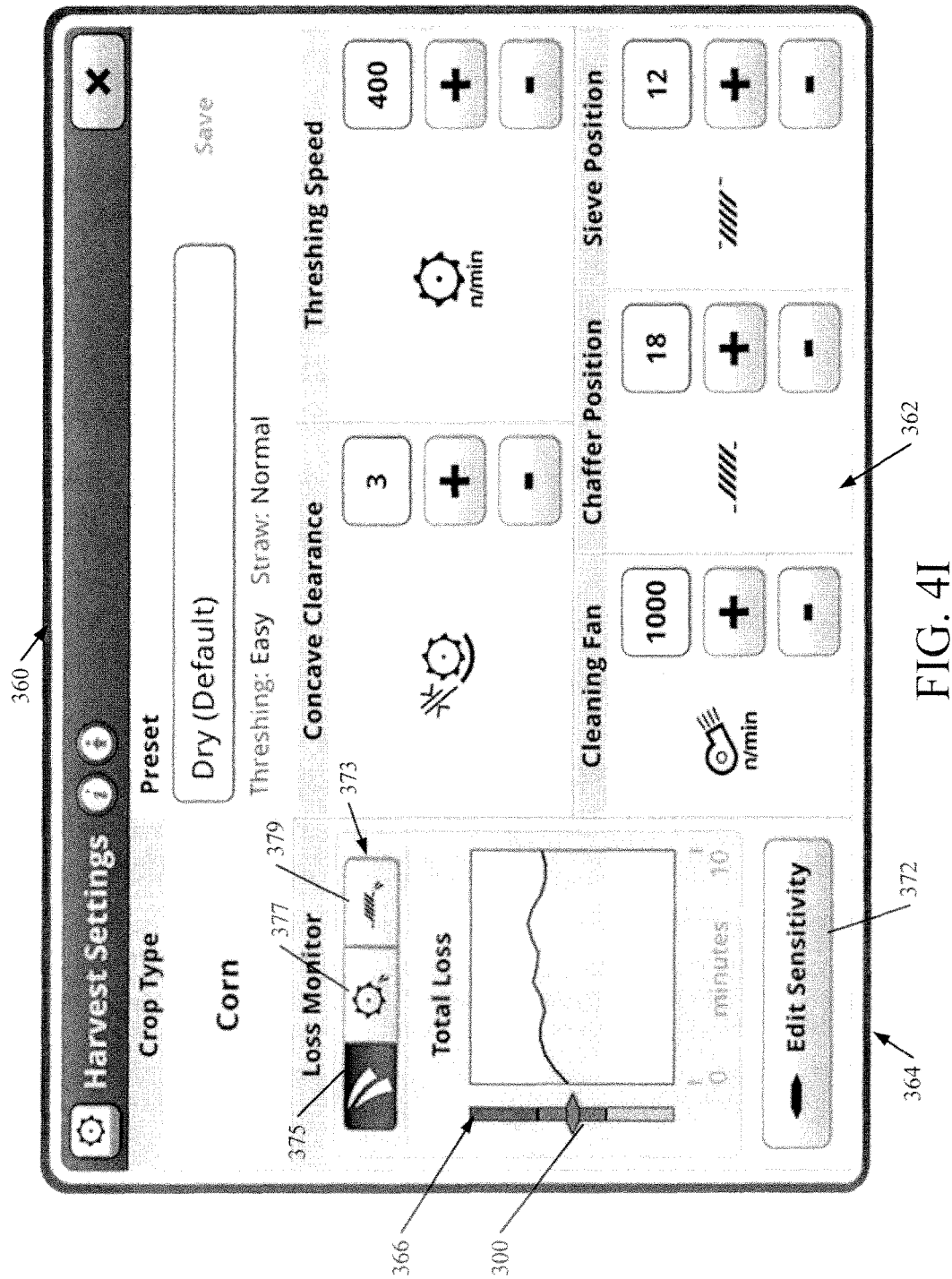

FIG. 4I shows another example of how grain loss can be displayed on a user interface display 360 on the 10-inch screen, for instance. It is similar to display 360 shown in FIG. 4H, and similar items are similarly numbered. FIG. 4I shows that display portion 364 can include a toggle user input mechanism 373 that can be actuated by the user to show total loss, shoe loss or separator loss, individually, on the time history graph. For instance, FIG. 4I shows an example in which the user has actuated total loss button 375. Thus, the total loss is displayed on the time history graph. If, on the other hand, the user actuates either of buttons 377 or 379, then the corresponding individual loss sensed by the shoe loss sensors 146 or separator loss sensors 148 is displayed on the time history graph.

Referring again to the flow diagram of FIG. 3, as harvesting continues, the currently sensed loss data is stored and used to generate the historic loss indicator 302. Processing reverts back to block 250, where a new set of sensor signals is received and processed to obtain a new, currently detected loss level that is used to display loss indicator 300. Continuing in this way is indicated by block 380 in FIG. 3.

When harvesting is completed, processing continues at block 382 where all of the sensed crop loss data can be output. It can be stored (either remotely or locally) for later access, as indicated by block 384. It can be output to a wide variety of remote systems as indicated by block 386. It can be output to a variety of other systems and in a variety of other ways as well, and this is indicated by block 388.

It should be noted that the discussion provided above is provided for the sake of example only. A wide variety of different changes can be made to those examples. For instance, and by way of example only, while the historical loss display element 302 is shown as a line, it could be shown as a set of discrete points. The colors associated with the different ranges on the display can be a wide variety of different colors as well. For instance, a yellow range may indicate that the grain loss is below the desired target range. A green range may indicate that the grain loss is within the desired target range, and a red range may indicate that the grain loss is above the expected target range. All of these are examples only. In addition, while the horizontal axis is shown as being displayed with respect to time, it could be displayed with respect to distance traveled by machine 102, or other variables as well. In addition, while the present discussion has proceeded with respect to the historical grain loss being displayed along a horizontal axis, it can be displayed along a vertical axis as well. In that case, the instantaneous grain loss indicator 300 can be displayed along a horizontal axis and the historical loss indicator 302 can run in the vertical direction, instead of the horizontal direction. Further, while the historical display has been shown aging as it moves to the right, the direction could be reversed so that it ages as it moves to the left. In addition, instead of displaying a single overall loss measurement (both instantaneous and historic), multiple different losses can be displayed on the same display. For instance, each of the different sensor signals can be used to generate a corresponding instantaneous display element displaying their current loss level, along with a historical display element indicating the historical loss detected by that individual sensor. These can be displayed on the same display screen, simultaneously, or they can be displayed separately, in which case the user may be able to toggle through them or view them in other ways. All of these examples, and other examples, are contemplated herein.

Also, the present discussion has mentioned processors and servers. In one example, the processors and servers include computer processors with associated memory and timing circuitry, not separately shown. They are functional parts of the systems or devices to which they belong and are activated by, and facilitate the functionality of the other components or items in those systems.

Also, a number of user interface displays have been discussed. They can take a wide variety of different forms and can have a wide variety of different user actuatable input mechanisms disposed thereon. For instance, the user actuatable input mechanisms can be text boxes, check boxes, icons, links, drop-down menus, search boxes, etc. They can also be actuated in a wide variety of different ways. For instance, they can be actuated using a point and click device (such as a track ball or mouse). They can be actuated using hardware buttons, switches, a joystick or keyboard, thumb switches or thumb pads, etc. They can also be actuated using a virtual keyboard or other virtual actuators. In addition, where the screen on which they are displayed is a touch sensitive screen, they can be actuated using touch gestures. Also, where the device that displays them has speech recognition components, they can be actuated using speech commands.

A number of data stores have also been discussed. It will be noted they can each be broken into multiple data stores. All can be local to the systems accessing them, all can be remote, or some can be local while others are remote. All of these configurations are contemplated herein.

Also, the figures show a number of blocks with functionality ascribed to each block. It will be noted that fewer blocks can be used so the functionality is performed by fewer components. Also, more blocks can be used with the functionality distributed among more components.

Figure 5:
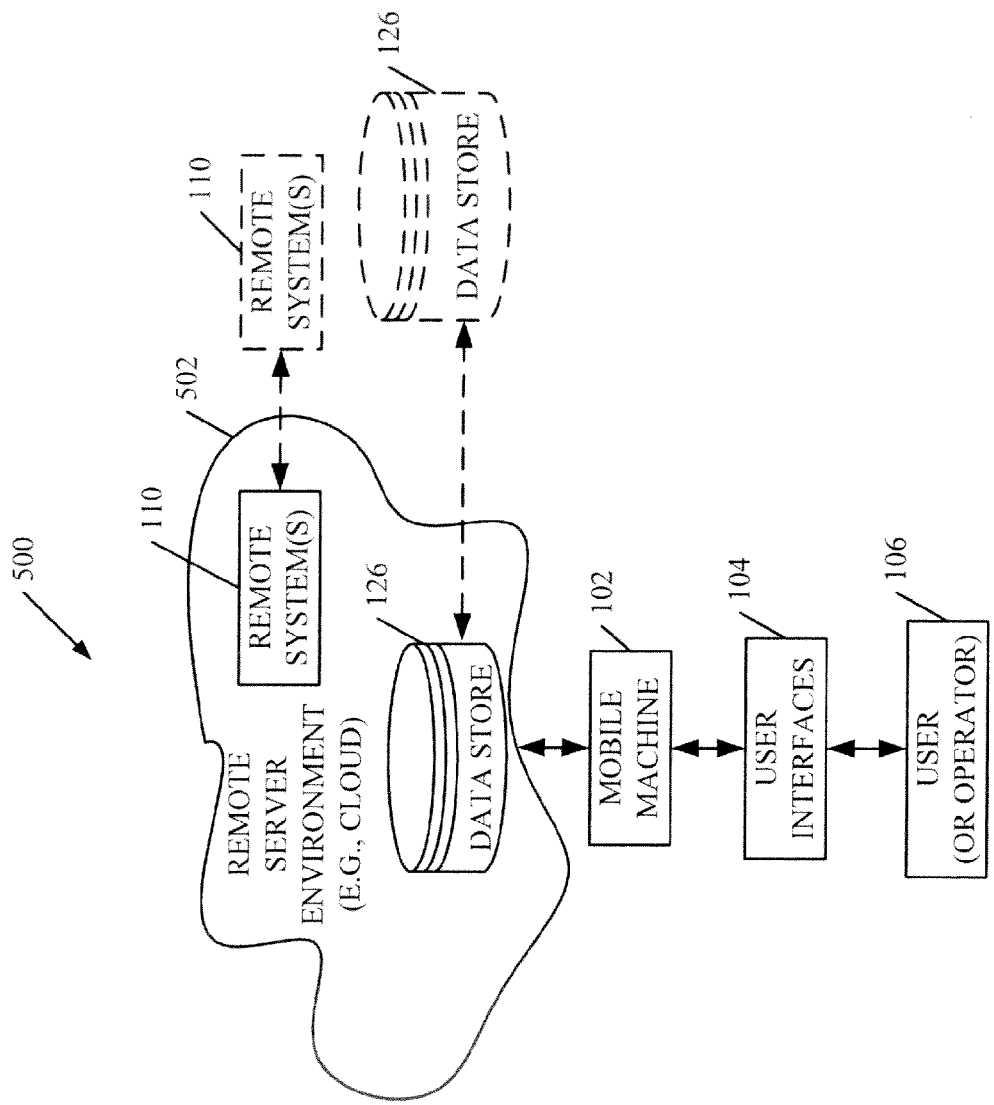
FIG. 5 shows one example of a remote server environment.

FIG. 5 is a block diagram of mobile machine 102, shown in FIG. 1, except that it communicates with elements in a remote server architecture 500. In an example embodiment, remote server architecture 500 can provide computation, software, data access, and storage services that do not require end-user knowledge of the physical location or configuration of the system that delivers the services. In various embodiments, remote servers can deliver the services over a wide area network, such as the internet, using appropriate protocols. For instance, remote servers can deliver applications over a wide area network and they can be accessed through a web browser or any other computing component. Software or components shown in FIG. 1 as well as the corresponding data, can be stored on servers at a remote location. The computing resources in a remote server environment can be consolidated at a remote data center location or they can be dispersed. Remote server infrastructures can deliver services through shared data centers, even though they appear as a single point of access for the user. Thus, the components and functions described herein can be provided from a remote server at a remote location using a remote server architecture. Alternatively, they can be provided from a conventional server, or they can be installed on client devices directly, or in other ways.

In the example shown in FIG. 5, some items are similar to those shown in FIG. 1 and they are similarly numbered. FIG. 5 specifically shows that data store 126 and remote systems 110 can be located at a remote server location 502. Therefore, mobile machine 102 accesses those systems through remote server location 502.

FIG. 5 also depicts another example of a remote server architecture. FIG. 5 shows that it is also contemplated that some elements of FIG. 1 are disposed at remote server location 502 while others are not. By way of example, data store 126 or remote system(s) 110 can be disposed at a location separate from location 502, and accessed through the remote server at location 502. Regardless of where they are located, they can be accessed directly by mobile machine 102, through a network (either a wide area network or a local area network), they can be hosted at a remote site by a service, or they can be provided as a service, or accessed by a connection service that resides in a remote location. Also, the data can be stored in substantially any location and intermittently accessed by, or forwarded to, interested parties. For instance, physical carriers can be used instead of, or in addition to, electromagnetic wave carriers. In such an embodiment, where cell coverage is poor or nonexistent, another mobile machine (such as a fuel truck) can have an automated information collection system. As the mobile machine 102 comes close to the fuel truck for fueling, the system automatically collects the information from the mobile machine 102 using any type of ad-hoc wireless connection. The collected information can then be forwarded to the main network as the fuel truck reaches a location where there is cellular coverage (or other wireless coverage). For instance, the fuel truck may enter a covered location when traveling to fuel other machines or when at a main fuel storage location. All of these architectures are contemplated herein. Further, the information can be stored on the mobile machine 102 until it enters a covered location. The mobile machine 102, itself, can then send the information to the main network.

It will also be noted that the elements of FIG. 1, or portions of them, can be disposed on a wide variety of different devices. Some of those devices include servers, desktop computers, laptop computers, tablet computers, or other mobile devices, such as palm top computers, cell phones, smart phones, multimedia players, personal digital assistants, etc.

Figure 6:
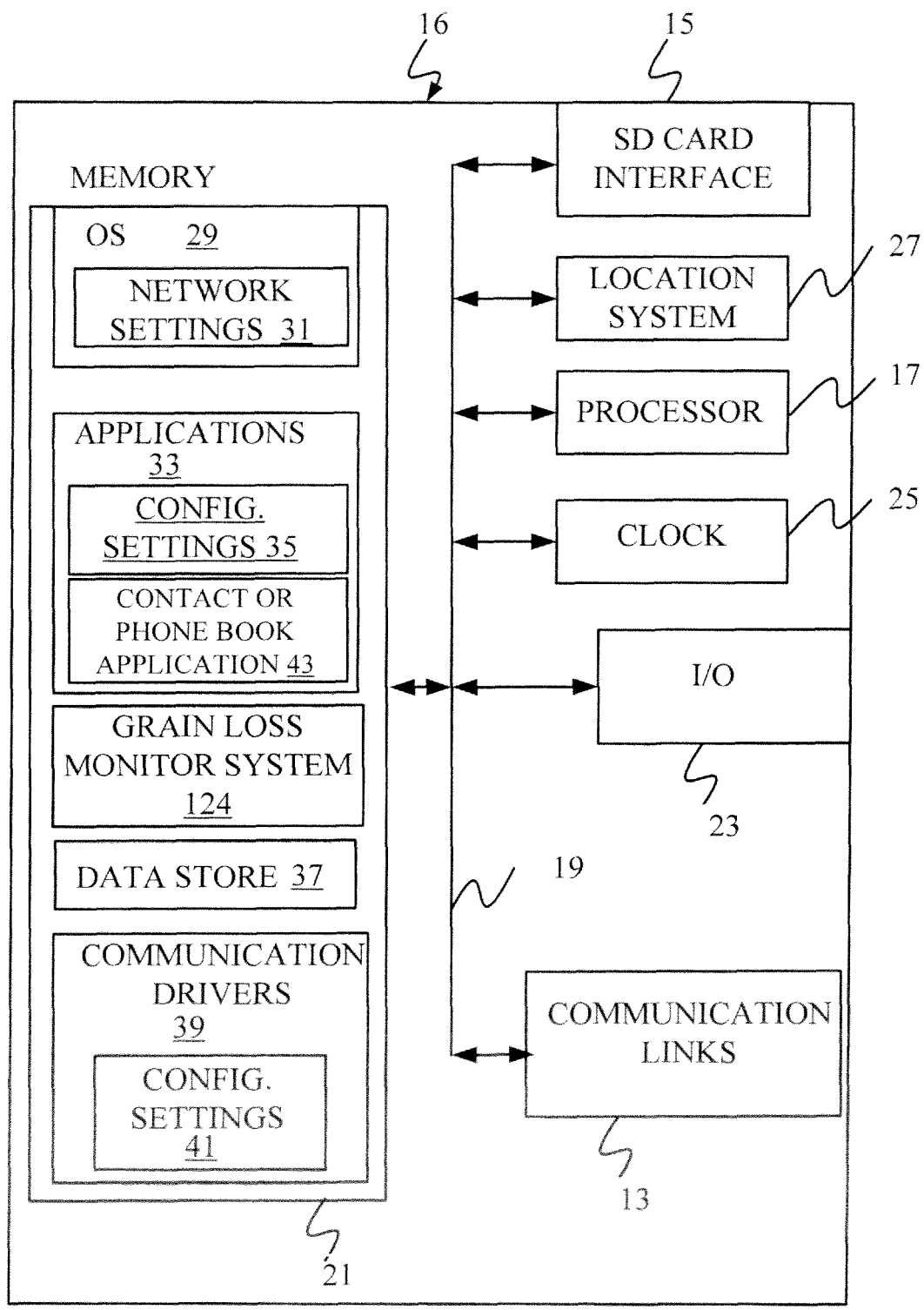
FIGS. 6-8 show examples of mobile devices that can be used in the architectures shown above.
Figure 7:
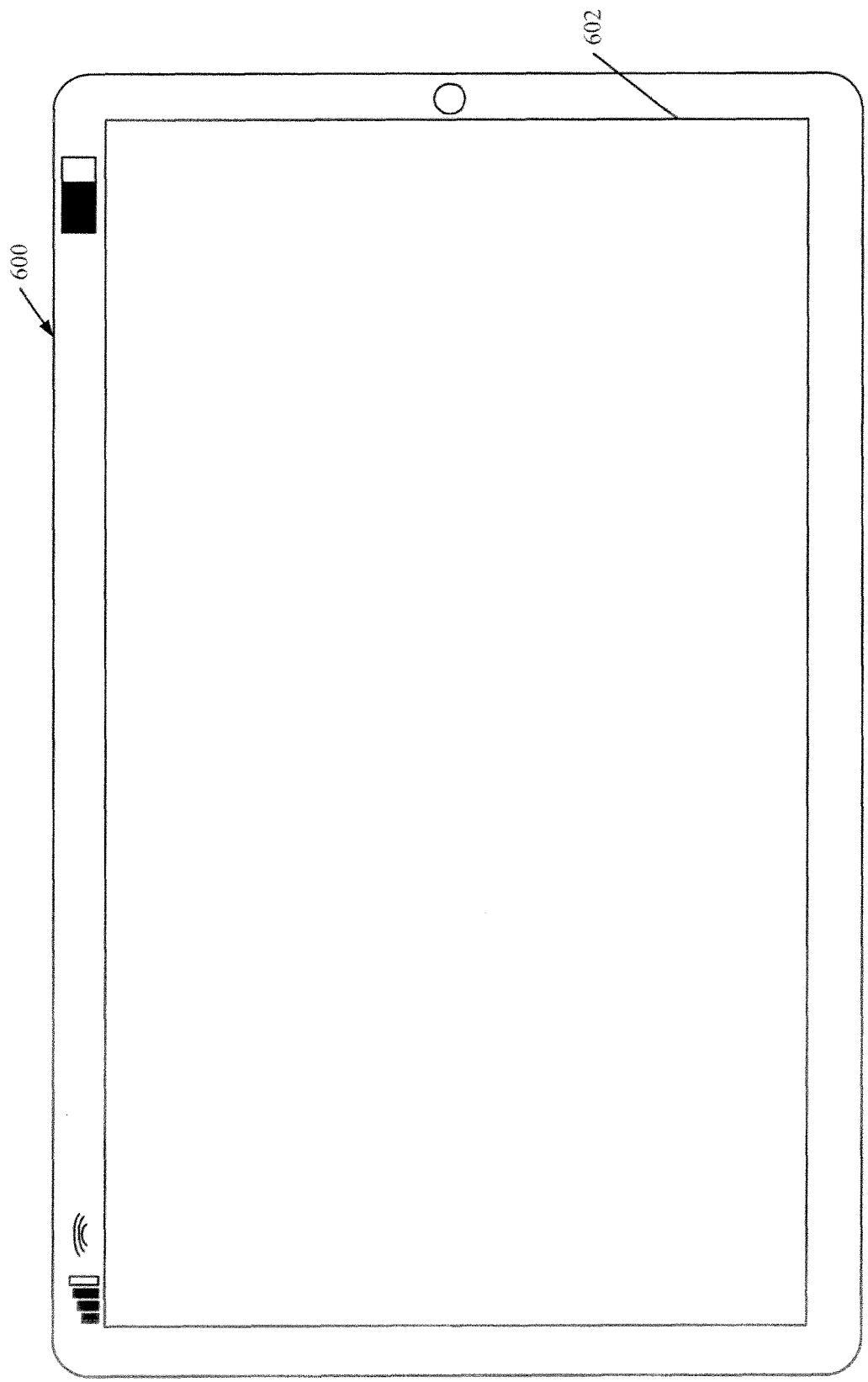
Figure 8:
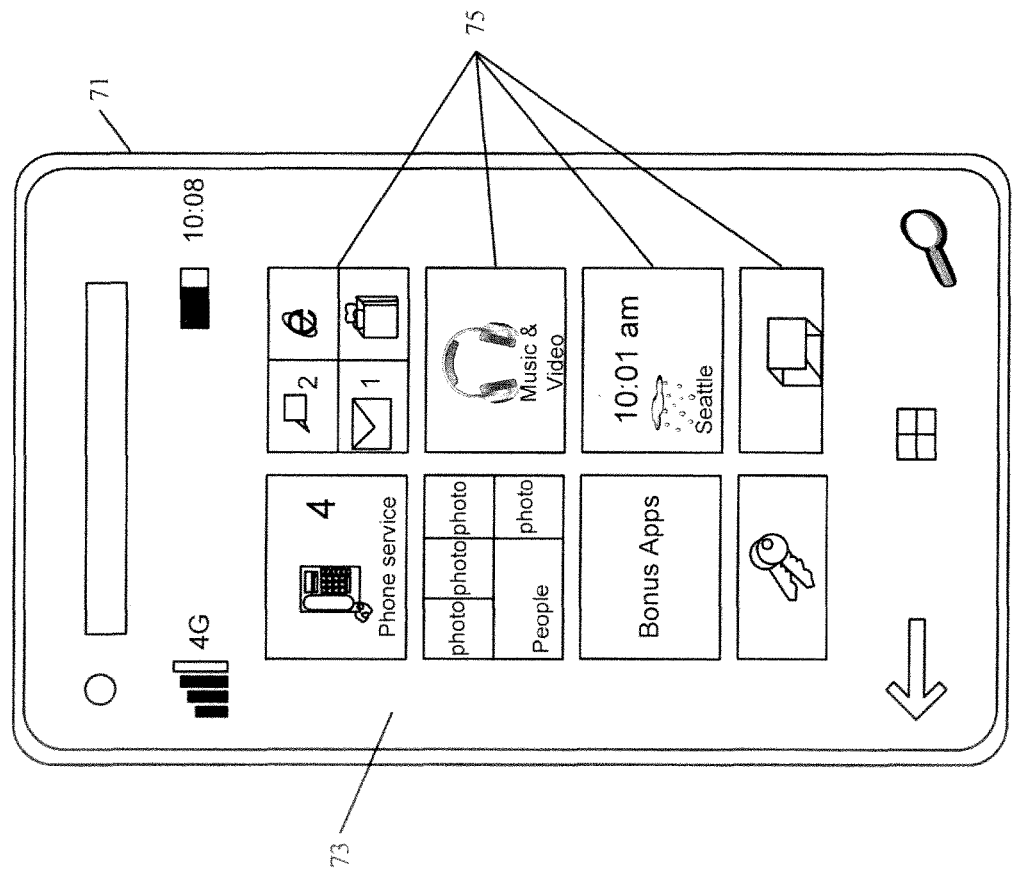

FIG. 6 is a simplified block diagram of one illustrative embodiment of a handheld or mobile computing device that can be used as a user's or client's hand held device 16, in which the present system (or parts of it) can be deployed. For instance, a mobile device can be deployed in the operator compartment of mobile machine 102 for use in generating, processing, or displaying the crop loss display. FIGS. 7-8 are examples of handheld or mobile devices.

FIG. 6 provides a general block diagram of the components of a client device 16 that can run some components shown in FIG. 1, that interacts with them, or both. In the device 16, a communications link 13 is provided that allows the handheld device to communicate with other computing devices and under some embodiments provides a channel for receiving information automatically, such as by scanning. Examples of communications link 13 include allowing communication though one or more communication protocols, such as wireless services used to provide cellular access to a network, as well as protocols that provide local wireless connections to networks.

Under other examples, applications can be received on a removable Secure Digital (SD) card that is connected to an interface 15. Interface 15 and communication links 13 communicate with a processor 17 (which can also embody processor 116 from FIG. 1) along a bus 19 that is also connected to memory 21 and input/output (I/O) components 23, as well as clock 25 and location system 27.

I/O components 23, in one embodiment, are provided to facilitate input and output operations. I/O components 23 for various embodiments of the device 16 can include input components such as buttons, touch sensors, optical sensors, microphones, touch screens, proximity sensors, accelerometers, orientation sensors and output components such as a display device, a speaker, and or a printer port. Other I/O components 23 can be used as well.

Clock 25 illustratively comprises a real time clock component that outputs a time and date. It can also, illustratively, provide timing functions for processor 17.

Location system 27 illustratively includes a component that outputs a current geographical location of device 16. This can include, for instance, a global positioning system (GPS) receiver, a LORAN system, a dead reckoning system, a cellular triangulation system, or other positioning system. It can also include, for example, mapping software or navigation software that generates desired maps, navigation routes and other geographic functions.

Memory 21 stores operating system 29, network settings 31, applications 33, application configuration settings 35, data store 37, communication drivers 39, and communication configuration settings 41. Memory 21 can include all types of tangible volatile and non-volatile computer-readable memory devices. It can also include computer storage media (described below). Memory 21 stores computer readable instructions that, when executed by processor 17, cause the processor to perform computer-implemented steps or functions according to the instructions. Processor 17 can be activated by other components to facilitate their functionality as well.

FIG. 7 shows one example in which device 16 is a tablet computer 600. In FIG. 7, computer 600 is shown with user interface display screen 602. Screen 602 can be a touch screen or a pen-enabled interface that receives inputs from a pen or stylus. It can also use an on-screen virtual keyboard. Of course, it might also be attached to a keyboard or other user input device through a suitable attachment mechanism, such as a wireless link or USB port, for instance. Computer 600 can also illustratively receive voice inputs as well. Screen 602 can be used to display the crop loss display.

FIG. 8 shows the phone is a smart phone 71. Smart phone 71 has a touch sensitive display 73 that displays icons or tiles or other user input mechanisms 75. Mechanisms 75 can be used by a user to run applications, make calls, perform data transfer operations, etc. In general, smart phone 71 is built on a mobile operating system and offers more advanced computing capability and connectivity than a feature phone.

Note that other forms of the devices 16 are possible.

Figure 9:
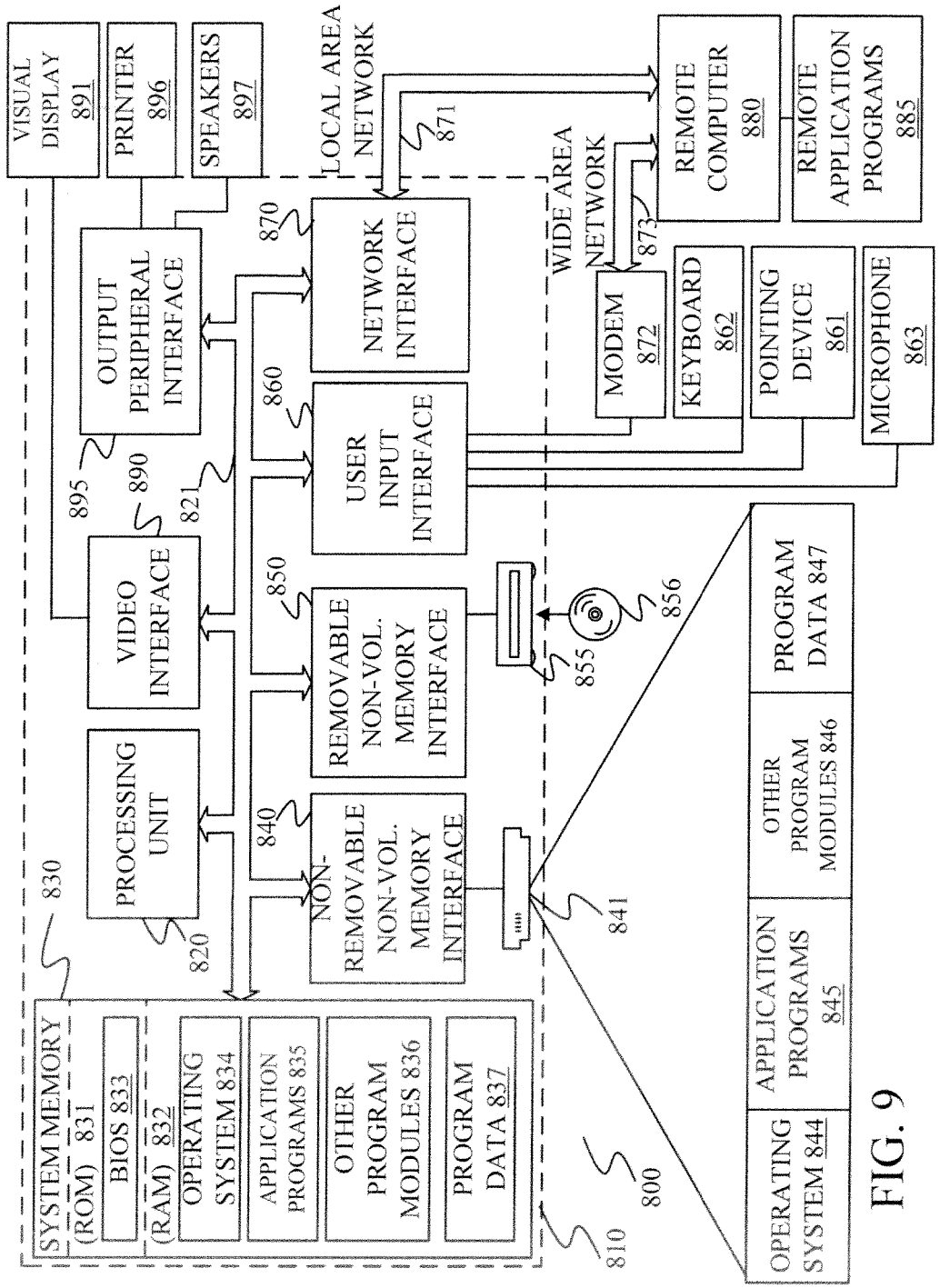
FIG. 9 is a block diagram of one example of a computing environment that can be deployed in any of the architectures shown above.

FIG. 9 is one example of a computing environment in which elements of FIG. 1, or parts of it, (for example) can be deployed. With reference to FIG. 9, an example system for implementing some embodiments includes a general-purpose computing device in the form of a computer 810. Components of computer 810 may include, but are not limited to, a processing unit 820 (which can comprise processor 116), a system memory 830, and a system bus 821 that couples various system components including the system memory to the processing unit 820. The system bus 821 may be any of several types of bus structures including a memory bus or memory controller, a peripheral bus, and a local bus using any of a variety of bus architectures. Memory and programs described with respect to FIG. 1 can be deployed in corresponding portions of FIG. 9.

Computer 810 typically includes a variety of computer readable media. Computer readable media can be any available media that can be accessed by computer 810 and includes both volatile and nonvolatile media, removable and non-removable media. By way of example, and not limitation, computer readable media may comprise computer storage media and communication media. Computer storage media is different from, and does not include, a modulated data signal or carrier wave. It includes hardware storage media including both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computer 810. Communication media may embody computer readable instructions, data structures, program modules or other data in a transport mechanism and includes any information delivery media. The term "modulated data signal" means a signal that has one or more of its characteristics set or changed in such a manner as to encode information in the signal.

The system memory 830 includes computer storage media in the form of volatile and/or nonvolatile memory such as read only memory (ROM) 831 and random access memory (RAM) 832. A basic input/output system 833 (BIOS), containing the basic routines that help to transfer information between elements within computer 810, such as during start-up, is typically stored in ROM 831. RAM 832 typically contains data and/or program modules that are immediately accessible to and/or presently being operated on by processing unit 820. By way of example, and not limitation, FIG. 9 illustrates operating system 834, application programs 835, other program modules 836, and program data 837.

The computer 810 may also include other removable/non-removable volatile/nonvolatile computer storage media. By way of example only, FIG. 9 illustrates a hard disk drive 841 that reads from or writes to non-removable, nonvolatile magnetic medianonvolatile magnetic disk 852, an optical disk drive 855, and nonvolatile optical disk 856. The hard disk drive 841 is typically connected to the system bus 821 through a non-removable memory interface such as interface 840, and optical disk drive 855 are typically connected to the system bus 821 by a removable memory interface, such as interface 850.

Alternatively, or in addition, the functionality described herein can be performed, at least in part, by one or more hardware logic components. For example, and without limitation, illustrative types of hardware logic components that can be used include Field-programmable Gate Arrays (FPGAs), Program-specific Integrated Circuits (e.g., ASICs), Program-specific Standard Products (e.g., ASSPs), System-on-a-chip systems (SOCs), Complex Programmable Logic Devices (CPLDs), etc.

The drives and their associated computer storage media discussed above and illustrated in FIG. 9, provide storage of computer readable instructions, data structures, program modules and other data for the computer 810. In FIG. 9, for example, hard disk drive 841 is illustrated as storing operating system 844, application programs 845, other program modules 846, and program data 847. Note that these components can either be the same as or different from operating system 834, application programs 835, other program modules 836, and program data 837.

A user may enter commands and information into the computer 810 through input devices such as a keyboard 862, a microphone 863, and a pointing device 861, such as a mouse, trackball or touch pad. Other input devices (not shown) may include a joystick, game pad, satellite dish, scanner, or the like. These and other input devices are often connected to the processing unit 820 through a user input interface 860 that is coupled to the system bus, but may be connected by other interface and bus structures. A visual display 891 or other type of display device is also connected to the system bus 821 via an interface, such as a video interface 890. In addition to the monitor, computers may also include other peripheral output devices such as speakers 897 and printer 896, which may be connected through an output peripheral interface 895.

The computer 810 is operated in a networked environment using logical connections (such as a local area network—LAN, or wide area network WAN) to one or more remote computers, such as a remote computer 880.

When used in a LAN networking environment, the computer 810 is connected to the LAN 871 through a network interface or adapter 870. When used in a WAN networking environment, the computer 810 typically includes a modem 872 or other means for establishing communications over the WAN 873, such as the Internet. In a networked environment, program modules may be stored in a remote memory storage device. FIG. 9 illustrates, for example, that remote application programs 885 can reside on remote computer 880.

It should also be noted that the different embodiments described herein can be combined in different ways. That is, parts of one or more embodiments can be combined with parts of one or more other embodiments. All of this is contemplated herein.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A computing system, comprising:
 a plurality of crop loss sensors on a mobile machine that generate a plurality of crop loss sensor signals, the plurality of crop loss sensors comprising:
  a first crop loss sensor that provides a first crop loss sensor signal indicative of grain loss at a cleaning shoe of the mobile machine; and
  a second crop loss sensor that provides a second crop loss sensor signal indicative of grain loss at a separator of the mobile machine;
 a display device on the mobile machine;
 a loss aggregator component that receives the plurality of crop loss sensor signals from the plurality of crop loss sensors and generates a crop loss metric, based on the plurality of crop loss sensor signals and a contribution value for each of the plurality of crop loss sensor signals, wherein the crop loss metric is indicative of an aggregate crop loss sensed by the plurality of crop loss sensors and indicated by the contribution values for the plurality of crop loss sensor signals;
 a balance setting component that, in response to user actuation of a balance adjustment user input mechanism, adjusts the contribution value for at least one of the plurality of crop loss sensor signals;
 a first crop loss display generator that generates a first crop loss display element based on the crop loss metric and controls the display device to display the first crop loss display element relative to a target loss range indicator indicative of a target loss range; and
 a historic crop loss display generator that generates a historic crop loss display element, based on previously generated crop loss metrics, and controls the display device to display the historic crop loss display element relative to the target loss range indicator and relative to the first crop loss display element.

2. The computing system of claim 1 and further comprising:
 a level setting component that generates a level setting user input mechanism that is actuated to modify the target loss range to include the first crop loss display element.

3. The computing system of claim 2 wherein the level setting component controls the display device to visually move the first crop loss display element to be displayed within the target loss range indicator in response to the actuation of the level setting user input mechanism.

4. The computing system of claim 1 wherein the historic crop loss display generator generates the historic crop loss display element as a substantially continuous display element that is indicative of the previously generated crop loss metrics.

5. The computing system of claim 4 wherein the historic crop loss display generator generates the historic crop loss display element that is substantially continuous over time.

6. The computing system of claim 4 wherein the plurality of crop loss sensors are disposed on a mobile harvester that moves over a field and wherein the historic crop loss display generator generates the historic crop loss display element that is substantially continuous over displacement of the mobile harvester across the field.

7. The computing system of claim 4 wherein the historic crop loss display generator generates the substantially continuous display element as a continuous line display element.

8. The computing system of claim 4 wherein the historic crop loss display generator generates the substantially continuous display element as a series of discrete display elements.

9. The computing system of claim 1 and further comprising:
 an individual sensor display component that, in response to user actuation of a multiple sensor user input mechanism, controls the display device to display on a given display screen, a plurality of sensor display elements, each displaying a sensor display corresponding to a crop loss level sensed by a different one of the plurality of crop loss sensors.

10. The computing system of claim 1 wherein the first crop loss display generator and the historic crop loss display generator control the display device to display the first crop loss display element and the historic crop loss display element, respectively, proximate an axis that has a given resolution and further comprising:
 a sensitivity adjustment component that, in response to user actuation of a sensitivity adjustment user input mechanism, adjusts the resolution on the axis.

11. A method, comprising:
 sensing crop loss at a plurality of different points in a mobile harvesting machine; generating a crop loss signal indicative of the sensed crop loss, wherein generating a crop loss signal comprises generating a different crop loss signal corresponding to the crop loss sensed at each of the plurality of different points, and wherein generating a crop loss metric comprises generating the crop loss metric as a current aggregate loss measure indicative of an aggregate crop loss sensed at the plurality of different points on the mobile harvesting machine;

generating a crop loss metric indicative of the sensed crop loss based on the crop loss signal;

generating a first crop loss display element based on the crop loss metric;

controlling a display device of the mobile harvesting machine to display the first crop loss display element relative to a target loss range indicator indicative of a target loss range;

generating a historic crop loss display element, based on previously generated crop loss metrics;

detecting user actuation of a level setting user input mechanism and in response, controlling the display device to visually move the first crop loss display element to be displayed within visual boundaries of the target loss range indicator indicative of an upper and lower target value; and controlling the display device of the mobile harvesting machine to display the historic crop loss display element relative to the target loss indicator and relative to the first crop loss display element.

12. The method of claim 11 wherein generating the historic crop loss display element comprises:

displaying the historic crop loss display element as a substantially continuous display element that is indicative of the previously generated crop loss metrics.

13. The method of claim 11 and further comprising:

detecting user actuation of a multiple sensor user input mechanism; and in response, controlling the display device to display a plurality of sensor display elements, each displaying a sensor display corresponding to a crop loss level sensed by a different one of a plurality of crop loss sensors, each sensor display element displayed on a separate graphical display.

14. A mobile machine, comprising:

a crop harvesting mechanism;

a plurality of different crop loss sensors that each generate a different crop loss sensor signal and sense crop loss in the crop harvesting mechanism and that each generate one of a plurality of crop loss signals indicative of the sensed crop loss;

a display device of the mobile machine;

a loss aggregator component that receives the plurality of crop loss sensor signals and generates a crop loss metric as a current aggregate loss measure indicative of an aggregate crop loss sensed by the plurality of crop loss sensors and indicated by the plurality of crop loss sensor signals;

a first crop loss display generator that generates a first crop loss display element based on the crop loss metric and controls the display device to display the first crop loss display element relative to a target loss range indicator indicative of a target loss range; and a historic crop loss display generator that generates a historic crop loss display element, based on previously generated crop loss metrics, and controls the display device to display the historic crop loss display element relative to the target loss indicator and relative to the first crop loss display element.

15. The mobile machine of claim 14 and further comprising:

a level setting component that generates a level setting user input mechanism and controls the display device to visually move the first crop loss display element to be displayed within the target loss range indicator in response to an actuation of the level setting user input mechanism.

* * * * *